(12) United States Patent
Himmelsbach et al.

(10) Patent No.: US 6,627,634 B2
(45) Date of Patent: Sep. 30, 2003

(54) BICYCLIC HETEROCYCLES, PHARMACEUTICAL COMPOSITIONS CONTAINING THEM, THEIR USE, AND PROCESSES FOR PREPARING THEM

(75) Inventors: Frank Himmelsbach, Mittelbiberach (DE); Elke Langkopf, Warthausen (DE); Birgit Jung, Schwabenheim (DE); Stefan Blech, Warthausen (DE); Flavio Solca, Vienna (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/816,003

(22) Filed: Mar. 23, 2001

(65) Prior Publication Data
US 2001/0044435 A1 Nov. 22, 2001

Related U.S. Application Data
(60) Provisional application No. 60/199,706, filed on Apr. 26, 2000.

(30) Foreign Application Priority Data

Apr. 8, 2000 (DE) .......................................... 100 17 539
Aug. 18, 2000 (DE) .......................................... 100 40 525

(51) Int. Cl.$^7$ ....................... A61K 31/517; A61P 35/00; C07D 513/00; C07D 413/00; C07D 401/00
(52) U.S. Cl. ............................... 514/266.22; 514/266.1; 514/266.2; 514/266.23; 514/234.05; 514/212.02; 540/543; 544/70; 544/116; 544/283; 544/284; 544/290; 544/293
(58) Field of Search ........................ 514/266.1, 266.2, 514/266.22, 266.23, 234.5, 212.02; 544/283, 284, 290, 293, 70, 116; 540/543

(56) References Cited

U.S. PATENT DOCUMENTS 6,399,602 B1 * 6/2002 Barker et al. ............ 514/234.5

FOREIGN PATENT DOCUMENTS

| WO | WO99/06396 A1 | 2/1993 |
| WO | WO97/38983 A1 | 10/1997 |
| WO | WO98/43960 A1 | 10/1998 |
| WO | WO99/09016 A1 | 2/1999 |
| WO | WO00/18740 A1 | 4/2000 |

* cited by examiner

Primary Examiner—Richard L. Raymond
Assistant Examiner—Tamthom N. Truong
(74) Attorney, Agent, or Firm—Robert P. Raymond; Timothy X. Witkowski; Anthony P. Bottino

(57) ABSTRACT

Bicyclic heterocycles of general formula

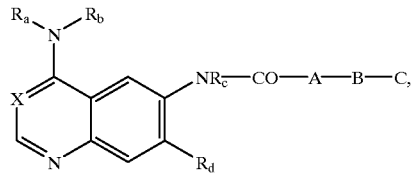

(I)

wherein:

$R_a$ to $R_d$, A to C and X are as defined herein, the tautomers, the stereoisomers and the salts thereof, particularly the physiologically acceptable salts thereof with inorganic or organic acids or bases, which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

9 Claims, No Drawings

BICYCLIC HETEROCYCLES, PHARMACEUTICAL COMPOSITIONS CONTAINING THEM, THEIR USE, AND PROCESSES FOR PREPARING THEM

RELATED APPLICATIONS

This application claims benefit under 35 U.S.C. §119(e) of prior U.S. provisional application Ser. No. 60/199,706, filed Apr. 26, 2000. U.S. provisional application Ser. No. 60/199,706 is hereby incorporated by reference herein in its entirety.

The present invention relates to bicyclic heterocycles of general formula

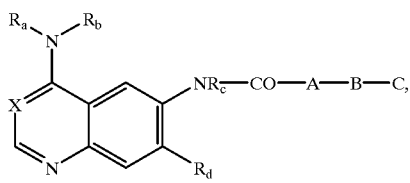

(I)

the tautomers, the stereoisomers and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

In the above general formula I

X denotes a methyne group substituted by a cyano group or a nitrogen atom, $R_a$ denotes a hydrogen atom or a $C_{1-4}$-alkyl group, $R_b$ denotes a phenyl, benzyl, or 1-phenylethyl group wherein the phenyl nucleus in each case is substituted by the groups $R_1$ to $R_3$, whilst $R_1$ and $R_2$, which may be identical or different, in each case denote a hydrogen, fluorine, chlorine, bromine, or iodine atom, a $C_{1-4}$-alkyl, hydroxy, $C_{1-4}$-alkoxy, $C_{3-6}$-cycloalkyl, $C_{4-6}$-cycloalkoxy, $C_{2-5}$-alkenyl, or $C_{2-5}$-alkynyl group, an aryl, aryloxy, arylmethyl, or arylmethoxy group, a $C_{3-5}$-alkenyloxy or $C_{3-5}$-alkynyloxy group, whilst the unsaturated moiety may not be linked to the oxygen atom, a $C_{1-4}$-alkylsulfenyl, $C_{1-4}$-alkylsulfinyl, $C_{1-4}$-alkylsulfonyl, $C_{1-4}$-alkylsulfonyloxy, trifluoromethylsulfenyl, trifluoromethylsulfinyl, or trifluoromethylsulfonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{1-4}$-alkyl groups, whilst the substituents may be identical or different, or $R_1$ together with $R_2$, if they are bound to adjacent carbon atoms, denote a —CH=CH—CH=CH—, —CH=CH—NH—, or —CH=N—NH— group, and $R_3$ denotes a hydrogen, fluorine, chlorine, or bromine atom, a $C_{1-4}$-alkyl, trifluoromethyl, or $C_{1-4}$-alkoxy group, $R_c$ denotes a hydrogen atom or a $C_{1-4}$-alkyl group, $R_d$ denotes a hydrogen atom, a $C_{1-6}$-alkoxy, $C_{4-7}$-cycloalkoxy, or $C_{3-7}$-cycloalkyl-$C_{1-4}$-alkoxy group, a $C_{2-6}$-alkoxy group, which is substituted from position 2 by a hydroxy, $C_{1-4}$-alkoxy, $C_{4-7}$-cycloalkoxy, $C_{3-7}$-cycloalkyl-$C_{1-3}$-alkoxy, di-($C_{1-4}$-alkyl)-amino, pyrrolidino, piperidino, morpholino, piperazino, or 4-($C_{1-4}$-alkyl)piperazino group, whilst the abovementioned cyclic imino groups may be substituted by one or two $C_{1-2}$-alkyl groups, a tetrahydrofuran-3-yloxy, tetrahydropyran-3-yloxy, tetrahydropyran-4-yloxy, tetrahydrofuranylmethoxy, or tetrahydropyranylmethoxy group, A denotes a 1,1- or 1,2-vinylene group optionally substituted by a methyl or trifluoromethyl group or by two methyl groups, a 1,3-butadien-1,4-ylene group optionally substituted by a methyl or trifluoromethyl group or by two methyl groups, or an ethynylene group, B denotes a $C_{1-6}$-alkylene group wherein one or two hydrogen atoms may be replaced by fluorine atoms, or, if B is bound to a carbon atom of group C, it may also denote a bond, C denotes a pyrrolidino group wherein the two hydrogen atoms in the 2 position are replaced by a group D, wherein D denotes a —$CH_2$—O—CO—$CH_2$—, —$CH_2CH_2$—O—CO—, —$CH_2$—O—CO—$CH_2CH_2$—, —$CH_2CH_2$—O—CO—$CH_2$—, or —$CH_2CH_2CH_2$—O—CO— bridge optionally substituted by one or two $C_{1-2}$-alkyl groups, a pyrrolidino group wherein the two hydrogen atoms in the 3 position are replaced by a group E, wherein E denotes an —O—CO—$CH_2CH_2$—, —$CH_2$—O—CO—$CH_2$—, —$CH_2CH_2$—O—CO—, —O—CO—$CH_2CH_2CH_2$—, —$CH_2$—O—CO—$CH_2CH_2$—, —$CH_2CH_2$—O—CO—$CH_2$—, —$CH_2CH_2CH_2$—O—CO—, —O—CO—$CH_2$—$NR_4$—$CH_2$—, —$CH_2$—O—CO—$CH_2$—$NR_4$—, —O—CO—$CH_2$—O—$CH_2$—, or —$CH_2$—O—CO—$CH_2$—O— bridge optionally substituted by one or two $C_{1-2}$-alkyl groups, whilst $R_4$ denotes a hydrogen atom or a $C_{1-4}$-alkyl group, a piperidino or hexahydroazepino group wherein the two hydrogen atoms in the 2 position are replaced by a group D, whilst D is as hereinbefore defined, a piperidino or hexahydroazepino group wherein the two hydrogen atoms in the 3 position or in the 4 position are replaced by a group E, whilst E is as hereinbefore defined, a piperazino or 4-($C_{1-4}$-alkyl)piperazino group wherein the two hydrogen atoms in the 2 position or in the 3 position of the piperazino ring are replaced by a group D, where D is as hereinbefore defined, a pyrrolidino or piperidino group wherein two vicinal hydrogen atoms are replaced by an —O—CO—$CH_2$—, —$CH_2$—O—CO—, —O—CO—$CH_2CH_2$—, —$CH_2$—O—CO—$CH_2$—, —$CH_2CH_2$—O—CO—, —O—CO—$CH_2$—$NR_4$—, or —O—CO—$CH_2$—O— bridge optionally substituted by one or two $C_{1-2}$-alkyl groups, whilst $R_4$ is as hereinbefore defined and the heteroatoms of the abovementioned bridges are not bound at the 2 or 5 position of the pyrrolidine ring and are not bound at the 2 or 6 position of the piperidino ring, a piperazino or 4-($C_{1-4}$-alkyl)piperazino group wherein a hydrogen atom in the 2 position together with a hydrogen atom in the 3 position of the piperazino ring are replaced by a —$CH_2$—O—CO—$CH_2$— or —$CH_2CH_2$—O—CO— bridge optionally substituted by one or two $C_{1-2}$-alkyl groups, a piperazino group wherein a hydrogen atom in the 3 position together with the hydrogen atom in the 4 position are replaced by a —CO—O—$CH_2CH_2$— or —$CH_2$—O—CO—$CH_2$— bridge optionally substituted by one or two $C_{1-2}$-alkyl groups, whilst in each case the left-hand end of the abovementioned bridges is bound to the 3 position of the piperazino ring, a pyrrolidino, piperidino, or hexahydroazepino group substituted by the group $R_5$, wherein $R_5$ denotes a 2-oxotetrahydrofuranyl, 2-oxotetrahydropyranyl, 2-oxo-1,4-dioxanyl, or 2-oxo-4-($C_{1-4}$-alkyl)-morpholinyl group optionally substituted by one or two $C_{1-2}$-alkyl groups, a pyrrolidino group substituted in the 3 position by a 2-oxomorpholino group, whilst the 2-oxomorpholino group may be substituted by one or two $C_{1-2}$-alkyl groups, a piperidino or hexahydroazepino group substituted in the 3 or 4 position by a 2-oxomorpholino group, whilst the 2-oxomorpholino group may be substituted by one or two $CH_{1-2}$-alkyl groups, a 4-($C_{1-4}$-alkyl)piperazino or 4-($C_{1-4}$-alkyl)-homopiperazino group substituted at a cyclic carbon atom by $R_5$, wherein $R_5$ is as hereinbefore defined, a piperazino or homopiperazino group substituted in the 4 position by the group $R_6$, wherein $R_6$ denotes a 2-oxotetrahydrofuran-3-yl, 2-oxotetrahydrofuran-4-yl, 2-oxotetrahydropyran-3-yl, 2-oxotetrahydropyran-4-yl, or 2-oxotetrahydropyran-5-yl group optionally substituted by one or two $C_{1-2}$-alkyl groups, a pyrrolidino group substituted in the 3 position by a ($R_4NR_6$), $R_6O$, $R_6S$, $R_6SO$, or $R_6SO_2$ group, whilst $R_4$ and $R_6$ are as hereinbefore defined, a piperidino or hexahydroazepino group substituted in the 3 or 4 position by an ($R_4NR_6$), $R_6O$, $R_6S$, $R_6SO$, or $P_6SO_2$ group wherein $R_4$ and $R_6$ are as hereinbefore defined, a pyrrolidino, piperidino, or hexahydroazepino group substituted by a $R_5$-$C_{1-4}$-alkyl, ($R_4NR_6$)—$C_{1-4}$-alkyl, $R_6O$—$C_{1-4}$-alkyl, $R_6S$—$C_{1-4}$-alkyl, $R_6SO$—$C_{1-4}$-alkyl, $R_6SO_2$—$C_{1-4}$-alkyl, or $R_4NR_6$—CO group wherein $R_4$ to $R_6$ are as hereinbefore defined, a pyrrolidino group substituted in the 3 position by a $R_5$—CO—$NR_4$, $R_5$—$C_{1-4}$-alkylene-$CONR_4$, ($R_4NR_6$)—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxomorpholino-$C_{1-4}$-alkylene-$CONR_4$, $R_5$—$C_{1-4}$-alkylene-Y, or $C_{2-4}$-alkyl-Y group, whilst the $C_{2-4}$-alkyl moiety of the $C_{2-4}$-alkyl-Y group is substituted in each case from position 2 by a ($R_4NR_6$), $R_6O$, $R_6S$, $R_6SO$, or $R_6SO_2$ group and the 2-oxomorpholino moiety may be substituted by one or two $C_{1-2}$-alkyl groups, wherein $R_4$ to $R_6$ are as hereinbefore defined, and Y denotes an oxygen or sulfur atom, an imino, N—($C_{1-4}$-alkyl)-imino, sulfinyl, or sulfonyl group, a piperidino or hexahydroazepino group substituted in the 3 or 4 position by a $R_5$—CO—$NR_4$, $R_5$—$C_{1-4}$-alkylene-$CONR_4$, ($R_4NR_6$)—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxomorpholino-$C_{1-4}$-alkylene-$CONR_4$, $R_5$—$C_{1-4}$-alkylene-Y, or $C_{2-4}$-alkyl-Y group wherein Y is as hereinbefore defined, the 2-oxomorpholino moiety may be substituted by one or two $C_{1-2}$-alkyl groups and the $C_{2-4}$-alkyl moiety of the $C_{2-4}$-alkyl-Y group is substituted in each case from position 2 by a ($R_4NR_6$), $R_6O$, $R_6S$, $R_6SO$, or $R_6SO_2$ group, whilst $R_4$ to $R_6$ are as hereinbefore defined, a 4-($C_{1-4}$-alkyl)piperazino or 4-($C_{1-4}$-alkyl)-homopiperazino group substituted at a cyclic carbon atom by an $R_5$—$C_{1-4}$-alkyl, ($R_4NR_6$)—$C_{1-4}$-alkyl, $R_6$—$C_{1-4}$-alkyl, $R_6S$—$C_{1-4}$-alkyl, $R_6SO$—$C_{1-4}$-alkyl, $R_6SO_2$—$C_{1-4}$-alkyl, or $R_4NR_6$—CO group, wherein $R_4$ to $R_6$ are as hereinbefore defined, a piperazino or homopiperazino group substituted in the 4 position by an $R_5$—$C_{1-4}$-alkyl, $R_5$—CO, $R_5$—$C_{1-4}$-alkylene-CO, ($R_4NR_6$)—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, or $R_6SO_2$—$C_{1-4}$-alkylene-CO group wherein $R_4$ to $R_6$ are as hereinbefore defined, a piperazino or homopiperazino group substituted in the 4 position by a $C_{2-4}$-alkyl group, wherein the $C_{2-4}$-alkyl group is substituted in each case from position 2 by an ($R_4NR_6$), $R_6O$, $R_6S$, $R_6SO$, or $R_6SO_2$ group, whilst $R_4$ and $R_6$ are as hereinbefore defined, a pyrrolidino, piperidino, or hexahydroazepino group substituted by a 2-oxomorpholino-$C_{1-4}$-alkyl group, wherein the 2-oxomorpholino moiety may be substituted by one or two $C_{1-2}$-alkyl groups, a pyrrolidino group substituted in the 3 position by a $C_{2-4}$-alkyl-Y group, wherein Y is as hereinbefore defined and the $C_{2-4}$-alkyl moiety of the $C_{2-4}$-alkyl-Y group is substituted in each case from position 2 by a 2-oxomorpholino group optionally substituted by one or two $C_{1-2}$-alkyl groups, a piperidino or hexahydroazepino group substituted in the 3 or 4 position by a $C_{2-4}$-alkyl-Y group wherein Y is as hereinbefore defined and the $C_{2-4}$-alkyl moiety of the $C_{2-4}$-alkyl-Y group is substituted in each case from position 2 by a 2-oxomorpholino group optionally substituted by one or two $C_{1-2}$-alkyl groups, a 4-($C_{1-4}$-alkyl)piperazino or 4-($C_{1-4}$-alkyl)-homopiperazino group substituted at a cyclic carbon atom by a 2-oxomorpholino-$C_{1-4}$-alkyl group, wherein the 2-oxomorpholino moiety may be substituted by one or two $C_{1-2}$-alkyl groups, a piperazino or homopiperazino group substituted in the 4 position by a 2-oxomorpholino-$C_{1-4}$-alkylene-CO group, wherein the 2-oxomorpholino moiety may be substituted by one or two $C_{1-2}$-alkyl groups, a piperazino or homopiperazino group substituted in the 4 position by a $C_{2-4}$-alkyl group, wherein the $C_{2-4}$-alkyl moiety is substituted in each case from position 2 by a 2-oxomorpholino group optionally substituted by one or two $C_{1-2}$-alkyl groups, a pyrrolidinyl or piperidinyl group substituted in the 1 position by the group $R_6$, by an $R_5$—$C_{1-4}$-alkyl, $R_5$13 CO, $R_5$—$C_{1-4}$-alkylene-CO, ($R_4NR_6$)—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO, or 2-oxomorpholino-$C_{1-4}$-alkylene-CO group wherein $R_4$ to $R_6$ are as hereinbefore defined and the 2-oxomorpholino moiety may be substituted by one or two $C_{1-2}$-alkyl groups, a pyrrolidinyl or piperidinyl group substituted in the 1 position by a $C_{2-4}$-alkyl group wherein the $C_{2-4}$-alkyl moiety is substituted in each case from position 2 by an $(R_4NR_6)$, $R_6O$, $R_6S$, $R_6SO$, $R_6SO_2$, or 2-oxomorpholino group, whilst $R_4$ and $R_6$ are as hereinbefore defined and the 2-oxomorpholino moiety may be substituted by one or two $C_{1-2}$-alkyl groups, a pyrrolidin-3-yl-$NR_4$, piperidin-3-yl-$NR_4$, or piperidin-4-yl-$NR_4$ group substituted in each case at the cyclic nitrogen atom by the group $R_6$, by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO, or 2-oxomorpholino-$C_{1-4}$-alkylene-CO group, wherein $R_4$ to $R_6$ are as hereinbefore defined and the 2-oxomorpholino moiety may be substituted by one or two $C_{1-2}$-alkyl groups, a pyrrolidin-3-yl-$NR_4$, piperidin-3-yl-$NR_4$, or piperidin-4-yl-$NR_4$ group substituted in each case at the cyclic nitrogen atom by a $C_{2-4}$-alkyl group, wherein the $C_{2-4}$-alkyl moiety is substituted in each case from position 2 by an $(R_4NR_6)$, $R_6O$, $R_6S$, $R_6SO$, $R_6SO_2$, or 2-oxomorpholino group, whilst $R_4$ and $R_6$ are as hereinbefore defined and the 2-oxomorpholino moiety may be substituted by one or two $C_{1-2}$-alkyl groups, a $R_5$—$C_{1-4}$-alkylene-$NR_4$ group wherein $R_4$ and $R_5$ are as hereinbefore defined, or a $C_{2-4}$-alkyl-$NR_4$-group, wherein the $C_{2-4}$-alkyl moiety is substituted in each case from position 2 by an $(R_4NR_6)$, $R_6O$, $R_6S$, $R_6SO$, $R_6SO_2$, or 2-oxomorpholino group, whilst $R_4$ and $R_6$ are as hereinbefore defined and the 2-oxomorpholino moiety may be substituted by one or two $C_{1-2}$-alkyl groups, while by the abovementioned aryl moieties is meant a phenyl group which may in each case be mono- or disubstituted by R', while the substituents may be identical or different and R' denotes a fluorine, chlorine, bromine, or iodine atom, a $C_{1-2}$-alkyl, trifluoromethyl, or $C_{1-2}$-alkoxy group or two groups R', if they are bound to adjacent carbon atoms, together denote a $C_{3-4}$-alkylene, methylenedioxy, or 1,3-butadien-1,4-ylene group.

Preferred compounds of the above general formula I are those wherein

X denotes a nitrogen atom, $R_a$ denotes a hydrogen atom, $R_b$ denotes a phenyl, benzyl, or 1-phenylethyl group wherein the phenyl nucleus is substituted in each case by the groups $R_1$ to $R_3$, whilst
  $R_1$ and $R_2$, which may be identical or different, in each case denote a methyl group or a hydrogen, fluorine, chlorine, or bromine atom and
  $R_3$ denotes a hydrogen atom, $R_c$ denotes a hydrogen atom, $R_d$ denotes a hydrogen atom, a methoxy, ethoxy, $C_{4-6}$-cycloalkoxy, $C_{3-6}$-cycloalkylmethoxy, 2-methoxyethoxy, 2-(cyclobutyloxy)ethoxy, 2-(cyclopentyloxy)ethoxy, 2-(cyclohexyloxy)ethoxy, 2-(cyclopropylmethoxy)ethoxy, tetrahydrofuran-3-yloxy, tetrahydropyran-4-yloxy, tetrahydrofuran-2-ylmethoxy, tetrahydrofuran-3-ylmethoxy, tetrahydropyran-2-ylmethoxy, or tetrahydropyran-4-ylmethoxy group, A denotes a 1,2-vinylene group, B denotes a methylene or ethylene group or, if B is bound to a carbon atom of group C, it may also denote a bond, C denotes a pyrrolidino group wherein the two hydrogen atoms in the 3 position are replaced by a group E, wherein
  E denotes a —O—CO—$CH_2CH_2$—, —$CH_2$—O—CO—$CH_2$—, —$CH_2CH_2$—O—CO—, —$CH_2CH_2$—O—CO—$CH_2$—, —O—CO—$CH_2$—$NR_4$—$CH_2$—, —$CH_2$—O—CO—$CH_2$—$NR_4$—, —O—CO—$CH_2$—O—$CH_2$—, or —$CH_2$—O—CO—$CH_2$—O— bridge optionally substituted by one or two methyl groups,
  where $R_4$ denotes a methyl or ethyl group, a piperidino group wherein the two hydrogen atoms in the 3 position or in the 4 position are replaced by a group E, where E is as hereinbefore defined, a pyrrolidino or piperidino group wherein two vicinal hydrogen atoms are replaced by an —O—CO—$CH_2$—, —$CH_2$—O—CO—, —O—CO—$CH_2$—$NR_4$—, or —O—CO—$CH_2$—O— bridge optionally substituted by one or two methyl groups, whilst $R_4$ is as hereinbefore defined and the heteroatoms of the abovementioned bridges are not bound at the 2 or 5 position of the pyrrolidine ring and are not bound at the 2 or 6 position of the piperidino ring, a piperazino group wherein a hydrogen atom in the 3 position together with the hydrogen atom in the 4 position are replaced by a —CO—O—$CH_2CH_2$— or —$CH_2$—O—CO—$CH_2$— bridge optionally substituted by one or two methyl groups, whilst in each case the left-hand end of the abovementioned bridges is bound to the 3 position of the piperazino ring, a pyrrolidino or piperidino group substituted by the group $R_5$, wherein
  $R_5$ denotes a 2-oxotetrahydrofuranyl, 2-oxo-1,4-dioxanyl, or 2-oxo-4-($C_{1-4}$-alkyl)-morpholinyl group optionally substituted by one or two methyl groups, a pyrrolidino group substituted in the 3 position by a 2-oxomorpholino group, whilst the 2-oxomorpholino group may be substituted by one or two methyl groups, a piperidino group substituted in the 3 or 4 position by a 2-oxomorpholino group, whilst the 2-oxomorpholino group may be substituted by one or two methyl groups, a piperazino group substituted in the 4 position by the group $R_6$, wherein
  $R_6$ denotes a 2-oxotetrahydrofuran-3-yl or 2-oxotetrahydrofuran-4-yl group optionally substituted by one or two methyl groups, a pyrrolidino group substituted in the 3 position by an $(R_4NR_6)$, $R_6O$, $R_6S$, $R_6SO$, or $R_6SO_2$ group, whilst $R_4$ and $R_6$ are as hereinbefore defined, a piperidino group substituted in the 3 or 4 position by an $(R_4NR_6)$, $R_6O$, $R_6S$, $R_6SO$, or $R_6SO_2$ group, whilst $R_4$ and $R_6$ are as hereinbefore defined, a pyrrolidino or piperidino group substituted by an $(R_4NR6)$—$C_{1-2}$-alkyl, $HNR_6$—CO, or $R_4NR_6$—CO group, whilst $R_4$ and $R_6$ are as hereinbefore defined, a pyrrolidino group substituted in the 3 position by an $R_5$—CO—NH or $R_5$—CO—$NR_4$ group, whilst $R_4$ and $R_5$ are as hereinbefore defined, a piperidino group substituted in the 3 or 4 position by an $R_5$—CO—NH or $R_5$—CO—$NR_4$ group, whilst $R_4$ and $R_5$ are as hereinbefore defined, a piperazino group substituted in the 4 position by an $R_5$—$C_{1-2}$-alkyl, $R_5$—CO, $R_5$—$C_{1-2}$-alkylene-CO, $(R_4NR_6)$—$C_{1-2}$-alkylene-CO, $R_6O$—$C_{1-2}$-alkylene-CO, $R_6S$—$C_{1-2}$-alkylene-CO, $R_6SO$—$C_{1-2}$-alkylene-CO, or $R_6SO_2$—$C_{1-2}$-alkylene-CO group wherein $R_4$ to $R_6$ are as hereinbefore defined, a piperazino group substituted in the 4 position by a $C_{2-3}$-alkyl group wherein the $C_{2-3}$-alkyl group is substituted in each case from position 2 by an $(R_4NR_6)$, $R_6O$, $R_6S$, $R_6SO$, or $R_6SO_2$ group, where $R_4$ and $R_6$ are as hereinbefore defined, a pyrrolidino or piperidino group substituted by a 2-oxomorpholino-$C_{1-2}$-alkyl group wherein the 2-oxomorpholino moiety may be substituted by one or two methyl groups, a piperazino group substituted in the 4 position by a 2-oxomorpholino-$C_{1-2}$-alkylene-CO group wherein the 2-oxomorpholino moiety may be substituted by one or two methyl groups, a piperazino group substituted in the 4 position by a $C_{2-3}$-alkyl group wherein the $C_{2-3}$-alkyl moiety is substituted in each case from position 2 by a 2-oxomorpholino group optionally substituted by one or two methyl groups, a piperidinyl group substituted in the 1 position by the group $R_6$, by an $R_5$—$C_{1-2}$-alkyl, $R_5$—CO, $R_5$—$C_{1-2}$-alkylene-CO, $(R_4NR_6)$—$C_{1-2}$-alkylene-CO, $R_6O$—$C_{1-2}$-alkylene-CO, $R_6S$—$C_{1-2}$-alkylene-CO, $R_6SO$—$C_{1-2}$-alkylene-CO, $R_6SO_2$—$C_{1-2}$-alkylene-CO, or 2-oxomorpholino-$C_{1-2}$-alkylene-CO group, whilst $R_4$ to $R_6$ are as hereinbefore defined and the 2-oxomorpholino moiety may be substituted by one or two methyl groups, a piperidinyl group substituted in the 1 position by a $C_{2-3}$-alkyl group wherein the $C_{2-3}$-alkyl moiety is substituted in each case from position 2 by an $(R_4NR_6)$, $R_6O$, $R_6S$, $R_6SO$, $R_6SO_2$, or 2-oxomorpholino group, whilst $R_4$ and $R_6$ are as hereinbefore defined and the 2-oxomorpholino moiety may be substituted by one or two methyl groups, a pyrrolidin-3-yl-$NR_4$, piperidin-3-yl-$NR_4$, or piperidin-4-yl-$NR_4$ group substituted in each case at the cyclic nitrogen atom by the group $R_6$, by an $R_5$—$C_{1-2}$-alkyl, $R_5$—CO, $R_5$—$C_{1-2}$-alkylene-CO, $(R_4NR_6)$—$C_{1-2}$-alkylene-CO, $R_6O$—$C_{1-2}$-alkylene-CO, $R_6S$—$C_{1-2}$-alkylene-CO, $R_6SO$—$C_{1-2}$-alkylene-CO, $R_6SO_2$—$C_{1-2}$-alkylene-CO, or 2-oxomorpholino-$C_{1-2}$-alkylene-CO group, wherein $R_4$ to $R_6$ are as hereinbefore defined and the 2-oxomorpholino moiety may be substituted by one or two methyl groups, or a pyrrolidin-3-yl-$NR_4$, piperidin-3-yl-$NR_4$, or piperidin-4-yl-NR4 group substituted in each case at the cyclic nitrogen atom by a $C_{2-3}$-alkyl group, wherein the $C_{2-3}$-alkyl moiety is substituted in each case from position 2 by an $(R_4NR_6)$, $R_6O$, $R_6S$, $R_6SO$, $R_6SO_2$, or 2-oxomorpholino group, whilst $R_4$ and $R_6$ are as hereinbefore defined and the 2-oxomorpholino moiety may be substituted by one or two methyl groups, the tautomers, the stereoisomers and the salts thereof.

Particularly preferred compounds of general formula I are those wherein

X denotes a nitrogen atom, $R_a$ denotes a hydrogen atom, $R_b$ denotes a phenyl, benzyl, or 1-phenylethyl group wherein the phenyl nucleus is substituted in each case by the groups $R_1$ to $R_3$, whilst $R_1$ and $R_2$, which may be identical or different, each denote a methyl group or a hydrogen, fluorine, chlorine, or bromine atom and $R_3$ denotes a hydrogen atom, $R_c$ denotes a hydrogen atom, $R_d$ denotes a hydrogen atom, a methoxy, ethoxy, $C_{4-6}$-cycloalkoxy, $C_{3-6}$-cycloalkylmethoxy, 2-methoxyethoxy, 2-(cyclobutyloxy)ethoxy, 2-(cyclopentyloxy)ethoxy, 2-(cyclohexyloxy)ethoxy, 2-(cyclopropylmethoxy)ethoxy, tetrahydrofuran-3-yloxy, tetrahydropyran-4-yloxy, tetrahydrofuran-2-ylmethoxy, tetrahydrofuran-3-ylmethoxy, tetrahydropyran-2-ylmethoxy, or tetrahydropyran-4-ylmethoxy group, A denotes a 1,2-vinylene group, B denotes a methylene or ethylene group or, if B is bound to a carbon atom of group C, it may also denote a bond, C denotes a piperidino group wherein the two hydrogen atoms in the 4 position are replaced by a —$CH_2$—O—CO—$CH_2$—, —$CH_2CH_2$—O—CO—, —$CH_2CH_2$—O—CO—$CH_2$—, —O—CO—$CH_2$—$NCH_3$—$CH_2$—, or —O—CO—$CH_2$—O—$CH_2$— bridge, a piperazino group wherein a hydrogen atom in the 3 position together with the hydrogen atom in the 4 position are replaced by a —CO—O—$CH_2$—$CH_2$— or —$CH_2$—O—CO—$CH_2$— bridge, whilst in each case the left-hand end of the above bridges is bound to the 3 position of the piperazino ring, a piperidino group substituted by a 2-oxotetrahydrofuranyl group, a piperidino group which is substituted in the 4 position by a 2-oxomorpholino or 2-oxomorpholinomethyl group, whilst the 2-oxomorpholino moiety may in each case be substituted by one or two methyl groups, a piperazino group which is substituted in the 4 position by a 2-oxotetrahydrofuran-3-yl or 2-oxotetrahydrofuran-4-yl group, a piperidino group which is substituted in the 4 position by a $CH_3NR_6$ or $R_6S$ group, whilst
 $R_6$ denotes a 2-oxotetrahydrofuran-3-yl or 2-oxotetrahydrofuran-4-yl group, a piperazino group which is substituted in the 4 position by a 2-oxotetrahydrofuranylmethyl or 2-oxotetrahydrofuranyl-carbonyl group, a piperazino group which is substituted in the 4 position by a straight-chained $C_{2-3}$-alkyl group, whilst the $C_{2-3}$-alkyl moiety is terminally substituted in each case by a 2-oxotetrahydrofuran-3-ylsulfenyl group, a piperidin-4-yl group which is substituted in the 1 position by a 2-oxotetrahydrofuran-3-yl or 2-oxotetrahydrofuran-4-yl group, or a piperidin-4-yl-$NCH_3$ group which is substituted at the cyclic nitrogen atom by a 2-oxotetrahydrofuran-3-yl, 2-oxotetrahydrofuran-4-yl, or 2-oxotetrahydrofuranylcarbonyl group, the tautomers, the stereoisomers and the salts thereof.

Most especially preferred compounds of the above general formula I are those wherein X denotes a nitrogen atom, $R_a$ denotes a hydrogen atom, $R_b$ denotes a 1-phenylethyl group or a phenyl group substituted by the groups $R_1$ to $R_3$, wherein $R_1$ and $R_2$, which may be identical or different, each denote a methyl group or a hydrogen, fluorine, chlorine, or bromine atom and $R_3$ denotes a hydrogen atom, $R_c$ denotes a hydrogen atom, $R_d$ denotes a hydrogen atom, a methoxy, ethoxy, 2-methoxy-ethoxy, cyclobutyloxy, cyclopentyloxy, cyclopropylmethoxy, cyclobutylmethoxy, tetrahydrofuran-3-yloxy, tetrahydropyran-4-yloxy, or tetrahydrofuran-2-ylmethoxy group, A denotes a 1,2-vinylene group, B denotes a methylene group or, if B is bound to a carbon atom of group C, it may also denote a bond, C denotes a piperidino group in which the two hydrogen atoms are replaced in the 4 position by a —CH₂—O—CO—CH₂—, —CH₂CH₂—O—CO—, —CH₂CH₂—O—CO—CH₂—, —O—CO—CH₂—NCH₃—CH₂—, or —O—CO—CH₂—O—CH₂— bridge, a piperazino group wherein a hydrogen atom in the 3 position together with the hydrogen atom in the 4 position are replaced by a —CO—O—CH₂—CH₂— or —CH₂—O—CO—CH₂— bridge, while in each case the left-hand end of the abovementioned bridges is bound to the 3 position of the piperazino ring, a piperidino group substituted by a 2-oxotetrahydrofuranyl group, a piperidino group which is substituted in the 4 position by a 2-oxomorpholino or 2-oxomorpholinomethyl group, while the 2-oxomorpholino moiety may in each case be substituted by one or two methyl groups, a piperazino group which is substituted in the 4 position by a 2-oxotetrahydrofuran-3-yl or 2-oxotetrahydrofuran-4-yl group, a piperidino group which is substituted in the 4 position by a $CH_3NR_6$ or $R_6S$ group, where $R_6$ denotes a 2-oxotetrahydrofuran-3-yl or 2-oxotetrahydrofuran-4-yl group, a piperazino group which is substituted in the 4 position by a 2-oxotetrahydrofuranylmethyl or 2-oxotetrahydrofuranylcarbonyl group, a piperazino group which is substituted in the 4 position by a [2-(2-oxotetrahydrofuran-3-ylsulfenyl)ethyl] group, a piperidin-4-yl group which is substituted in the 1 position by a 2-oxotetrahydrofuran-3-yl or 2-oxotetrahydrofuran-4-yl group, or a piperidin-4-yl-$NCH_3$ group which is substituted at the cyclic nitrogen atom by a 2-oxotetrahydrofuran-3-yl, 2-oxotetrahydrofuran-4-yl, or 2-oxotetrahydrofuranylcarbonyl group, the tautomers, the stereoisomers and the salts thereof.

The following are mentioned as most particularly preferred compounds of general formula I:

(a) 4-[(3-chloro-4-fluorophenyl)amino]-6-({4-[4-(2-oxotetrahydrofuran-3-yl)piperazin-1-yl]-1-oxo-2-buten-1-yl}amino)-7-cyclopropylmethoxyquinazoline, (b) 4-[(3-chloro-4-fluorophenyl)amino]-6-({4-[4-(2-oxotetrahydrofuran-4-yl)piperazin-1-yl]-1-oxo-2-buten-1-yl}amino)-7-cyclopropylmethoxyquinazoline, (c) 4-[(3-chloro-4-fluorophenyl)amino]-6-{[4-(4-{2-[(2-oxotetrahydrofuran-3-yl)sulfanyl]ethyl}piperazin-1-yl)-1-oxo-2-buten-1-yl]amino}-7-cyclopropylmethoxyquinazoline, (d) 4-[(3-chloro-4-fluorophenyl)amino]-6-{[4-(3-oxoperhydropyrazino[2,1-c][1,4]oxazin-8-yl)-1-oxo-2-buten-1-yl]amino}-7-cyclopropylmethoxyquinazoline, (e) (S)-4-[(3-chloro-4-fluorophenyl)amino]-6-[(4-{4-[(5-oxotetrahydrofuran-2-yl)carbonyl]piperazin-1-yl}-1-oxo-2-buten-1-yl)amino]-7-cyclopropylmethoxyquinazoline, (f) 4-[(3-chloro-4-fluorophenyl)amino]-6-{[4-(1-oxoperhydropyrazino[2,1-c][1,4]oxazin-8-yl)-1-oxo-2-buten-1-yl]amino}-7-cyclopropylmethoxyquinazoline and (g) 4-[(3-chloro-4-fluorophenyl)amino]-6-[(4-{4-[(2-oxotetrahydrofuran-3-yl)sulfanyl]piperidin-1-yl}-1-oxo-2-buten-1-yl)amino]-7-cyclopropylmethoxyquinazoline and the salts thereof.

The compounds of general formula I may be prepared, for example, by the following methods:

A. Reacting a Compound of General Formula

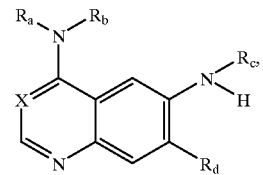

(II)

wherein:

$R_a$ to $R_d$ and X are as hereinbefore defined, with a compound of general formula

HO—CO—A—B—C (III)

wherein

A to C are as hereinbefore defined, or with the reactive derivatives thereof.

The reaction is optionally carried out in a solvent or mixture of solvents such as methylene chloride, dimethylformamide, benzene, toluene, chlorobenzene, tetrahydrofuran, or dioxane, optionally in the presence of a dehydrating agent, e.g., in the presence of isobutyl chloroformate, thionyl chloride, trimethyl chlorosilane, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, triphenylphosphine/carbon tetrachloride, or O-(benzotriazol-1-yl)-N,N,N',N'-tetramethyluronium tetrafluoroborate, or with a corresponding reactive derivative such as a corresponding ester, acid halide, or anhydride, optionally with the addition of an inorganic or organic base, preferably with the addition of an organic base such as triethylamine, N-ethyldiisopropylamine, or 4-dimethylaminopyridine, conveniently at temperatures between 0° C. and 150° C., preferably at temperatures between 0° C. and 80° C.

b. Reacting a Compound of General Formula

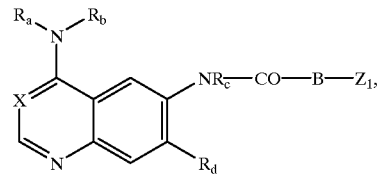

(IV)

optionally formed in the reaction mixture, wherein $R_a$ to $R_d$, A, B, and X are as hereinbefore defined, and $Z_1$, denotes an exchangeable group such as a halogen atom or a substituted sulfinyl or sulfonyl group, e.g., a chlorine or bromine atom, a methylsulfinyl, propylsulfinyl, phenylsulfinyl, benzylsulfinyl, methylsulfonyl, propylsulfonyl, phenylsulfonyl, or benzylsulfonyl group, with a compound of general formula

H—G  (V)

wherein

G denotes one of the groups mentioned for C hereinbefore which is linked to the group B via a nitrogen atom.

However, G may also denote a group which can be converted by lactonization into one of the groups mentioned for C hereinbefore, which are linked to the group B via a nitrogen atom (e.g., a correspondingly substituted gamma- or delta-hydroxycarboxylic acid ester group).

The reaction is conveniently carried out in a solvent such as isopropanol, butanol, tetrahydrofuran, dioxane, toluene, chlorobenzene, dimethylformamide, dimethylsulfoxide, methylene chloride, ethylene glycol monomethylether, ethylene glycol diethylether, or sulfolane, optionally in the presence of an inorganic or tertiary organic base, e.g., sodium carbonate or potassium hydroxide, a tertiary organic base, e.g., triethylamine, or in the presence of N-ethyldiisopropylamine (Hünig base), whilst these organic bases may simultaneously serve as the solvent, and optionally in the presence of a reaction accelerator such as an alkali metal halide at temperatures between −20° C. and 150° C., but preferably at temperatures between −10° C. and 100° C. The reaction may, however, also be carried out without a solvent or in an excess of the compound of general formula V used.

If G denotes a group which can be converted by lactonization into one of the groups mentioned for C hereinbefore which are linked to the group B via a nitrogen atom, cyclization to form the corresponding lactone may optionally follow. The cyclization to form the corresponding lactone is optionally carried out in a solvent such as acetonitrile, methylene chloride, tetrahydrofuran, dioxane, or toluene in the presence of an acid such as hydrochloric acid, p-toluenesulfonic acid, or trifluoroacetic acid at temperatures of between −10° C. and 120° C.

c. In order to prepare a compound of general formula I wherein C denotes one of the groups mentioned for C hereinbefore which contains an imino or $HNR_4$ group substituted by $R_6$ or by an $R_5$-$C_{1-4}$-alkyl group wherein $R_4$ to $R_6$ are as hereinbefore defined:

Reacting a Compound of General Formula

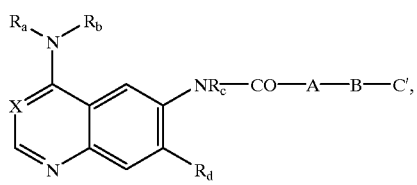

(VI)

wherein $R_a$ to $R_d$, A, and B are as hereinbefore defined, and

C' denotes one of the groups mentioned for C hereinbefore which contains a corresponding unsubstituted imino or $HNR_4$ group, where $R_4$ is as hereinbefore defined, with a compound of general formula $Z_2$—U  (VII)

wherein:

U denotes the group $R_6$ or a $R_5$-$C_{1-4}$-alkyl group, where $R_5$ and $R_6$ are as hereinbefore defined, and $Z_2$ denotes an exchangeable group such as a halogen atom or a substituted sulfonyloxy group, e.g., a chlorine or bromine atom, a methylsulfonyloxy, propylsulfonyloxy, phenylsulfonyloxy, or benzylsulfonyloxy group, or $Z_2$ together with an adjacent hydrogen atom denotes another carbon-carbon bond which is attached to a carbonyl group.

The reaction is conveniently carried out in a solvent such as methanol, ethanol, isopropanol, or acetonitrile and optionally in the presence of a base such as triethylamine, N-ethyldiisopropylamine, or 2-dimethylaminopyridine at temperatures between 0° C. and 100° C., but preferably at the boiling temperature of the reaction mixture.

If in a compound of general formula VII $Z_2$ denotes an exchangeable group, the reaction is preferably performed in a solvent or mixture of solvents such as methylene chloride, dimethylformamide, dimethylsulfoxide, sulfolane, benzene, toluene, chlorobenzene, tetrahydrofuran, benzene/tetrahydrofuran, or dioxane, conveniently in the presence of a tertiary organic base such as triethylamine or N-ethyldiisopropylamine (Hünig base), whilst these organic bases may simultaneously serve as the solvent, or in the presence of an inorganic base such as sodium carbonate, potassium carbonate, or sodium hydroxide solution, conveniently at temperatures between −20° C. and 200° C., preferably at temperatures between 0° C. and 150° C., or if in a compound of general formula VII $Z_2$ together with an adjacent hydrogen atom denotes another carbon-carbon bond attached to a carbonyl group, the reaction is preferably carried out in a solvent such as methanol, ethanol, isopropanol, or acetonitrile at temperatures between 0° C. and 100° C., but preferably at temperatures between 20° C. and the boiling temperature of the reaction mixture.

d. In order to prepare a compound of general formula I wherein C denotes one of the groups mentioned for C hereinbefore which contains an imino or $HNR_4$ group substituted by an $R_5CO$, $R_5$—$C_{1-4}$-alkylene-CO, ($R_4NR_6$)—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO, or 2-oxomorpholino-$C_{1-4}$-alkylene-CO group, where $R_4$ to $R_6$ are as hereinbefore defined and the 2-oxomorpholino moiety may be substituted by one or two $C_{1-2}$-alkyl groups:

Reacting a Compound of General Formula

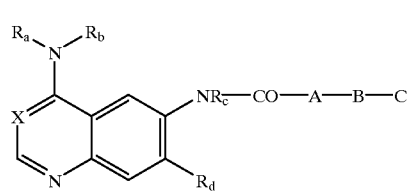

(VI)

wherein $R_a$ to $R_d$, A, and B are as hereinbefore defined, and

C' denotes one of the groups mentioned for C hereinbefore which contains a corresponding unsubstituted imino or $HNR_4$ group, where $R_4$ is as hereinbefore defined, with a compound of general formula

HO—CO—W  (VIII)

wherein

W denotes the group $R_5$ or a $R_5$—$C_{1-4}$-alkyl, $(R_4NR_6)$—$C_{1-4}$-alkyl, $R_6O$—$C_{1-4}$-alkyl, $R_6S$—$C_{1-4}$-alkyl, $R_6SO$—$C_{1-4}$-alkyl, $R_6SO_2$—$C_{1-4}$-alkyl, or 2-oxomorpholino-$C_{1-4}$-alkyl group, wherein $R_4$ to $R_6$ are as hereinbefore defined and the 2-oxomorpholino moiety may be substituted by one or two $C_{1-2}$-alkyl groups.

The reaction is optionally carried out in a solvent or mixture of solvents such as methylene chloride, dimethylformamide, benzene, toluene, chlorobenzene, tetrahydrofuran, or dioxane, optionally in the presence of a dehydrating agent, e.g., in the presence of isobutyl chloroformate, thionyl chloride, trimethyl chlorosilane, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, triphenylphosphine/carbon tetrachloride, or O-(benzotriazol-1-yl)-N,N,N',N'-tetramethyluronium tetrafluoroborate, or with a corresponding reactive derivative such as a corresponding ester, acid halide, or anhydride, optionally with the addition of an inorganic or organic base, preferably with the addition of an organic base such as triethylamine, N-ethyldiisopropylamine, or 4-dimethylaminopyridine, conveniently at temperatures between 0° C. and 150° C., preferably at temperatures between 0° C. and 80° C.

In the reactions described hereinbefore, any reactive groups present such as hydroxy, carboxy, amino, alkylamino, or imino groups may be protected during the reaction by conventional protecting groups which are cleaved again after the reaction.

For example, a protecting group for a hydroxy group may be a trimethylsilyl, acetyl, benzoyl, methyl, ethyl, tert-butyl, trityl, benzyl, or tetrahydropyranyl group, protecting groups for a carboxy group may be a trimethylsilyl, methyl, ethyl, tert-butyl, benzyl, or tetrahydropyranyl group, and protecting groups for an amino, alkylamino, or imino group may be a formyl, acetyl, trifluoroacetyl, ethoxycarbonyl, tert-butoxycarbonyl, benzyloxycarbonyl, benzyl, methoxy-benzyl, or 2,4-dimethoxybenzyl group and additionally, for the amino group, a phthalyl group.

Any protecting group used is optionally subsequently cleaved for example by hydrolysis in an aqueous solvent, e.g., in water, isopropanol/water, acetic acid/water, tetrahydrofuran/water, or dioxane/water, in the presence of an acid such as trifluoroacetic acid, hydrochloric acid, or sulfuric acid, or in the presence of an alkali metal base such as sodium hydroxide or potassium hydroxide, or aprotically, e.g., in the presence of iodotrimethylsilane, at temperatures between 0° C. and 120° C., preferably at temperatures between 10° C. and 100° C.

However, a benzyl, methoxybenzyl, or benzyloxycarbonyl group is cleaved, for example, hydrogenolytically, e.g., with hydrogen in the presence of a catalyst such as palladium/charcoal in a suitable solvent such as methanol, ethanol, ethyl acetate, or glacial acetic acid, optionally with the addition of an acid such as hydrochloric acid at temperatures between 0° C. and 100° C., but preferably at room temperatures between 20° C. and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert-butyl or tert-butyloxycarbonyl group is preferably cleaved by treating with an acid such as trifluoroacetic acid or hydrochloric acid or by treating with iodotrimethylsilane optionally using a solvent such as methylene chloride, dioxane, methanol, or diethyl ether.

A trifluoroacetyl group is preferably cleaved by treating with an acid such as hydrochloric acid, optionally in the presence of a solvent such as acetic acid at temperatures between 50° C. and 120° C. or by treating with sodium hydroxide solution optionally in the presence of a solvent such as tetrahydrofuran at temperatures between 0° C. and 50° C.

A phthalyl group is preferably cleaved in the presence of hydrazine or a primary amine such as methylamine, ethylamine, or n-butylamine in a solvent such as methanol, ethanol, isopropanol, toluene/water, or dioxane at temperatures between 20° C. and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf N. L. Allinger and E. L. Eliel in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g., by chromatography and/or fractional crystallization, and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms salts or derivatives such as e.g., esters or amides with the racemic compound, particularly acids and the activated derivatives or alcohols thereof, and separating the diastereomeric mixture of salts or derivatives thus obtained, e.g., on the basis of their differences in solubility, whilst the free antipodes may be released from the pure diastereomeric salts or derivatives by the action of suitable agents. Optically active acids in common use are e.g., the D- and L-forms of tartaric acid or dibenzoyltartaric acid, di-o-tolyltartaric acid, malic acid, mandelic acid, camphorsulfonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulfuric acid, phosphoric acid, fumaric acid, succinic acid, lactic acid, citric acid, tartaric acid, or maleic acid.

The compounds of general formulae II to VIII used as starting materials are known from the literature in some cases or may be obtained by methods known from the literature (cf. Examples I to XV).

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerization or tyrosine kinase itself. It is also possible that the transmission of signals to components located further along is blocked.

The biological properties of the new compounds were investigated as follows:

The inhibition of the EGF-R-mediated signal transmission can be demonstrated, e.g., with cells which express human EGF-R and whose survival and proliferation depend on stimulation by EGF or TGF-alpha. A cell line of murine origin dependent on interleukin-3-(IL-3) which was genetically modified to express functional human EGF-R was used here. The proliferation of these cells known as F/L-HERc can therefore be stimulated either by murine IL-3 or by EGF (cf. T. von Rüiden et al. in EMBO J. 7, 2749–2756 (1988) and J. H. Pierce et al. in Science 239, 628–631 (1988)).

The starting material used for the F/L-HERc cells was the cell line FDC-P$_1$, the production of which has been described by T. M. Dexter et al., J. Exp. Med. 152 1036–1047 (1980). Alternatively, however, other growth-factor-dependent cells may also be used (cf., e.g., J. H. Pierce et al., Science 239, 628–631 (1988); H. Shibuya et al., Cell 70, 57–67 (1992); and W. S. Alexander et al., EMBO J. 10, 3683–3691 (1991)). For expressing the human EGF-R cDNA (cf. A. Ullrich et al., Nature 309, 418–425 (1984)) recombinant retroviruses were used as described by T. von Rüiden et al., EMBO J. 7, 2749–2756 (1988), except that the retroviral vector LXSN (cf. A. D. Miller et al., BioTechniques 7, 980–990 (1989)) was used for the expression of the EGF-R cDNA and the line GP+E86 (cf. D. Markowitz et al., J. Virol. 62, 1120–1124 (1988)) was used as the packaging cell.

The test was performed as follows:

F/L-HERc cells were cultivated in RPMI/1640 medium (BioWhittaker), supplemented with 10% fetal calf serum (FCS, Boehringer Mannheim), 2 mM glutamine (BioWhittaker), standard antibiotics and 20 ng/ml of human EGF (Promega), at 37° C. and 5% $CO_2$. In order to investigate the inhibitory activity of the compounds according to the invention, $1.5 \times 10^4$ cells per well were cultivated in triplicate in 96-well dishes in the above medium (200 μl), the cell proliferation being stimulated with either EGF (20 ng/ml) or murine IL-3. The IL-3 used was obtained from culture supernatants of the cell line X63/0 mIL-3 (cf. H. Karasuyama et al., Eur. J. Immunol. 18, 97–104 (1988)). The compounds according to the invention were dissolved in 100% dimethylsulfoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer 96™ AQueous Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom. The following results were obtained:

| Compound (Example No.) | Inhibition of EGF-Dependent Proliferation $IC_{50}$ [nM] |
| --- | --- |
| 1 | 0.05 |
| 2 | 0.60 |
| 4 | 3 |
| 4(3) | 10 |

The compounds of general formula I according to the invention thus inhibit the signal transduction by tyrosine kinases, as demonstrated by the example of the human EGF receptor, and are therefore useful for treating pathophysiological processes caused by hyperfunction of tyrosine kinases. These are, e.g., benign or malignant tumors, particularly tumors of epithelial and neuroepithelial origin, metastasization and the abnormal proliferation of vascular endothelial cells (neoangiogenesis).

The compounds according to the invention are also useful for preventing and treating diseases of the airways and lungs which are accompanied by increased or altered production of mucus caused by stimulation of tyrosine kinases, e.g., in inflammatory diseases of the airways such as chronic bronchitis, chronic obstructive bronchitis, asthma, bronchiectasias, allergic or non-allergic rhinitis or sinusitis, cystic fibrosis, α1-antitrypsin deficiency, or coughs, pulmonary emphysema, pulmonary fibrosis, and hyperreactive airways.

The compounds are also suitable for treating diseases of the gastrointestinal tract and bile duct and gall bladder which are associated with disrupted activity of the tyrosine kinases, such as may be found, e.g., in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménetriér's disease, secreting adenomas and protein loss syndrome. The compounds are also suitable for treating nasal polyps and polyps of the gastrointestinal tract of various origins, such as, for example, villous or adenomatous polyps of the large bowel, but also polyps in familial polyposis coli, intestinal polyps in Gardner's syndrome, polyps throughout the entire gastrointestinal tract in Peutz-Jeghers Syndrome, inflammatory pseudopolyps, juvenile polyps, colitis cystica profunda, and pneumatosis cystoides intestinales.

Moreover, the compounds of general formula I and the physiologically acceptable salts thereof may be used to treat kidney diseases, particularly cystic changes as in cystic kidneys, for treating renal cysts which may be idiopathic in origin or which occur in syndromes such as, e.g., tubercular sclerosis, in von-Hippel-Lindau Syndrome, in nephronophthisis and spongy kidney and other diseases caused by abnormal functioning of tyrosine kinases such as, e.g., epidermal hyperproliferation (psoriasis), inflammatory processes, diseases of the immune system, hyperproliferation of hematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g., etoposide), mitosis inhibitors (e.g., vinblastine), compounds which interact with nucleic acids (e.g., cis-platin, cyclophosphamide, adriamycin), hormone antagonists (e.g., tamoxifen), inhibitors of metabolic processes (e.g., 5-FU etc.), cytokines (e.g., interferons), antibodies, etc. For treating respiratory tract diseases, these compounds may be used on their own or in conjunction with other therapeutic agents for the airways, such as substances with a secretolytic, broncholytic and/or anti-inflammatory activity. For treating diseases in the region of the gastrointestinal tract, these compounds may also be administered on their own or in conjunction with substances having an effect on motility or secretion or with anti-inflammatory substances. These combinations may be administered either simultaneously or sequentially.

These compounds may be administered either on their own or in conjunction with other active substances by intravenous, subcutaneous, intramuscular, intrarectal, intraperitoneal, or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearyl alcohol, carboxymethylcellulose, or fatty substances such as hard fat or suitable mixtures thereof in conventional galenic preparations such as plain or coated tablets, capsules, powders, suspensions, solutions, sprays, or suppositories.

The following Examples are intended to illustrate the present invention without restricting it.

Preparation of the Starting Compounds

EXAMPLE I

4-[(3-chloro-4-fluorophenyl)amino]-6-{[4-(piperazin-1-yl)-1-oxo-2-buten-1yl]amino}-7-cyclopropylmethoxyquinazoline 5 ml of trifluoroacetic acid is added dropwise to 1.80 g of 4-[(3-chloro-4-fluorophenyl)amino]-6-({4-[4-(tert-butyloxycarbonyl)piperazin-1-yl]-11-oxo-2-buten-1-yl}amino)-7-cyclopropylmethoxyquinazoline in 10 ml methylene chloride while cooling with an ice bath. After one hour, the ice bath is removed and the reaction mixture is stirred overnight at ambient temperature. The mixture is then evaporated to dryness, and the flask residue is divided between 150 ml methylene chloride/methanol (9:1) and 100 ml of 1N sodium hydroxide solution. The aqueous phase is extracted twice more with the mixture of solvents, and the combined organic phases are dried over magnesium sulfate and concentrated by evaporation. The brownish crude product reacted further without any more purification.

Yield: 1.32 g (88% of theory); $R_f$ value: 0.60 (Reversed phase ready-made TLC plate (E. Merck), acetonitrile/water/trifluoroacetic acid=50:50:1); mass spectrum (ESI$^+$): m/z=511, 513 [M+H]$^+$.

The following compounds are obtained analogously to Example I:

(1) N-{2-[(2-oxotetrahydrofuran-3-yl)sulfanyl]ethyl}piperazine×2 trifluoroacetic acid (The reaction mixture is concentrated by evaporation without aqueous working up.) $R_f$ value: 0.68 (Reversed phase ready-made TLC plate (E. Merck), acetonitrile/water/trifluoroacetic acid=50:50:1)

(2) 4-[(3-chloro-4-fluorophenyl)amino]-6-{[4-(4-methylaminopiperidin-1-yl)-1-oxo-2buten-1-yl]amino}-7-cyclopropylmethoxyquinazoline $R_f$ value: 0.50 (Reversed phase ready-made TLC plate (E. Merck), acetonitrile/water/trifluoroacetic acid=50:50:1); mass spectrum (ESI$^-$): m/z=537, 539 [M–H]$^-$.

(3) 4-[(3-chloro-4-fluorophenyl)amino]-6-{[3-(piperidin-4-yl)-1-oxo-2-propen-1-yl]amino}-7-cyclopropylmethoxyquinazoline $R_f$ value: 0.50 (Reversed phase ready-made TLC plate (E. Merck), acetonitrile/water/trifluoroacetic acid=50:50:1); mass spectrum (ESI$^-$): m/z=494, 496 [M–H]$^-$.

(4) Perhydropyrazino[2,1-c][1,4]oxazin-3-one×2 trifluoroacetic acid (The reaction mixture is concentrated by evaporation without aqueous working up.) Mass spectrum (ESI$^+$): m/z=157 [M+H]$^+$.

(5) 4-[(3-chloro-4-fluorophenyl)amino]-6-({4-[N-(piperidin-4-yl)-N-methylamino]-1-oxo-2-buten-yl}amino)-7-cyclopropylmethoxyquinazoline Mass spectrum (ESI$^-$): m/z=537, 539 [M–H]$^-$.

(6) Perhydropyrazino[2,1-c][1,4]oxazin-1-one×2 trifluoroacetic acid (The reaction mixture is concentrated by evaporation without aqueous working up.) Mass spectrum (ESI$^+$): m/z=157 [M+H]$^+$.

(7) 4-[(2-oxotetrahydrofuran-3-yl)sulfanyl]piperidine×1 trifluoroacetic acid (The reaction mixture is concentrated by evaporation without aqueous working up.) $R_f$ value: 0.57 (Reversed phase ready-made TLC plate (E. Merck), acetonitrile/water/trifluoroacetic acid 50:50:1); mass spectrum (ESI$^+$): m/z=202 [M+H]$^+$.

(8) 4-[(2-oxo-6,6-dimethylmorpholin-4-yl)methyl]piperidine×trifluoroacetic acid (The starting material, 1-(tert-butyloxycarbonyl)-4-[N-(ethoxycarbonylmethyl)-N-((2-hydroxy-2-methylpropyl)aminomethyl]piperidine, is obtained by reacting 1-(tert-butyloxycarbonyl)-4-(methanesulfonyloxymethyl)-piperidine with N-(ethoxycarbonylmethyl)-2-hydroxy-2-methylpropylamine). Mass spectrum (ESI$^+$): m/z=227 [M+H]$^+$.

EXAMPLE II

4-[(3-chloro-4-fluorophenyl)amino]-6-({4-[4-(tert-butyloxycarbonyl)piperazin-1-yl]-1-oxo-2-buten 1-yl}amino)-7-cyclopropylmethoxyquinazoline 4.7 ml of oxalyl chloride is added dropwise at ambient temperature to a solution of 4.51 g of 4-bromocrotonic acid in 100 ml of methylene chloride. After the addition of one drop of N,N-dimethylformamide, the reaction mixture is stirred for about another 45 minutes at ambient temperature until the development of gas has ceased. The solvent is then distilled off from the resulting acid chloride in vacuo. In the meantime, 7.00 g of 6-amino-4-[(3-chloro-4-fluorophenyl)amino]-7-cyclopropylmethoxyquinazoline and 10.2 ml of diisopropylethylamine in 250 ml of tetrahydrofuran are cooled to 0° C. in an ice bath. The crude acid chloride is taken up in 20 ml of methylene chloride and added dropwise within 5 minutes while cooling with an ice bath. The reaction mixture is stirred for 45 minutes at 0° C. and for one hour at ambient temperature, then a suspension of 18.17 g of tert-butyl piperazine-1-carboxylate in 5 ml of N,N-dimethylformamide is added. After another 48 hours stirring at ambient temperature, the solvent is distilled off in vacuo and the residue is divided between water and ethyl acetate. The aqueous phase is extracted with ethyl acetate, the combined organic extracts are washed with saturated sodium chloride solution, dried over magnesium sulfate and concentrated by evaporation. The crude product is purified by chromatography through a silica gel column with ethyl acetate/methanol (15:1 to 9:1).

Yield: 5.2 g (44% of theory); $R_f$ value: 0.42 (silica gel, methylene chloride/methanol=9:1); mass spectrum (ESI$^-$): m/z=609, 611 [M−H]$^-$.

The following compounds are obtained analogously to Example II:

(1) 4-[(3-chloro-4-fluorophenyl)amino]-6-[(4-{4-[N-(tert-butyloxycarbonyl)-N-methylamino]piperidin-1-yl}-1-oxo-2-buten-1-yl)amino]-7-cyclopropylmethoxyquinazoline $R_f$ value: 0.35 (silica gel, ethyl acetate/methanol=9:1); mass spectrum (ESI$^-$): m/z=637, 639 [M−H]$^-$.

(2) 4-[(3-chloro-4-fluorophenyl)amino]-6-[(4-{N-[1-(tert-butyloxycarbonyl)piperidine-4-yl]-N-methylamino}-1-oxo-2-buten-1-yl)amino]-7-cyclopropylmethoxyquinazoline $R_f$ value: 0.39 (silica gel, ethyl acetate/methanol=9:1); mass spectrum (ESI$^-$): m/z=637, 639 [M−H]$^-$.

EXAMPLE III 6-amino-4-[(3-chloro-4-fluorophenyl)amino]-7-cyclopropylmethoxyquinazoline 30.00 g of 4-[(3-chloro-4-fluorophenyl)amino]-7-cyclopropylmethoxy-6-nitroquinazoline are suspended in a mixture of 900 ml of ethanol, 120 ml of glacial acetic acid, and 300 ml of water. The suspension is refluxed, producing a clear solution. 17.24 g of iron powder is then carefully added batchwise, while the reaction mixture effervesces each time. About 15 minutes after it has all been added, a precipitate is formed. The reaction mixture is stirred for a further 15 minutes and then evaporated to dryness in vacuo. The residue in the flask is taken up in 1000 ml of methylene chloride/methanol (9:1) and combined with 30 ml of 33% aqueous ammonia solution. The iron slurry is filtered off and washed with methylene chloride:methanol (9:1). The brown filtrate is filtered through a silica gel pack and evaporated to dryness. The residue in the flask is stirred with 60 ml of diethylether, suction filtered and dried in the air.

Yield: 22.60 g (82% of theory); melting point: 208° C.; mass spectrum (ESI$^+$): m/z=359, 361 [M+H]$^+$.

EXAMPLE IV

4-[(3-chloro-4-fluorophenyl)amino]-7-cyclopropylmethoxy-6-nitroquinazoline 66.66 g of potassium tert-butoxide is added batchwise to 47.07 ml of cyclopropylmethanol in 500 ml of N,N-dimethylformamide while cooling with an ice bath, while the temperature is not allowed to exceed 12° C. The reaction mixture is stirred for another 30 minutes in the cooling bath, then 50.00 g of 4-[(3-chloro-4-fluorophenyl)amino]-7-fluoro-6-nitroquinazoline is added batchwise, whereupon the reaction mixture turns dark red and the temperature rises to not more than 15° C. The cooling bath is then removed and the reaction mixture is stirred for another hour at ambient temperature. To work it up, the reaction mixture is poured into 4000 ml of water and neutralized with about 210 ml of 2N hydrochloric acid. The precipitate formed is suction filtered, washed with water and dried at 40° C.

Yield: 60.47 g of crude product; $R_f$ value: 0.60 (silica gel, cyclohexane/ethyl acetate=1:1); mass spectrum (ESI$^-$): m/z=387, 389 [M−H]$^-$.

EXAMPLE V 1-(tert-butyloxycarbonyl)-4-{2-[(2-oxotetrahydrofuran-3-yl)sulfanyl]ethyl}piperazine 4.02 g of 1-(tert-butyloxycarbonyl)-4-[2-(methanesulfonyloxy)ethyl]piperazine dissolved in methylene chloride is added to a methanolic solution of 1.40 g of sodium-2-oxotetra-hydrofuran-3-thiolate (prepared by treating 3-[(methylcarbonyl)sulfanyl]tetrahydrofuran-2-one with sodium methoxide in methanol). 10 ml of N,N-dimethylformamide is then added and the reaction mixture is stirred for 2.5 hours at 50° C. For working up, 100 ml of ethyl acetate is added. The organic phase is separated off, washed with water and sodium chloride solution, dried over magnesium sulfate and concentrated by evaporation. The red oily crude product is reacted without any further purification.

Yield: 3.50 g (96% of theory); $R_f$ value: 0.48 (silica gel, methylene chloride/methanol=9:1); mass spectrum (ESI$^-$): m/z=329 [M−H]$^-$.

EXAMPLE VI 3-(piperidin-4-yl)dihydrofuran-2-one 3.60 g of 3-(1-benzylpiperidin-4-ylidene)dihydrofuran-2-one is dissolved in 40 ml of methanol, combined with 360 mg of palladium on active charcoal (10%), and hydrogenated at ambient temperature. After the calculated amount of hydrogen has been taken up, the catalyst is filtered off and the filtrate is concentrated by evaporation in vacuo. A colorless oil remains, which is reacted without any further purification.

$R_f$ value: 0.16 (silica gel, ethyl acetate/methanol=9:1); mass spectrum (EI): m/z=169 [M]$^+$.

The following compounds are obtained analogously to Example VI:

(1) 4-[N-(tert-butyloxycarbonylmethyl)-N-(2-hydroxyethyl)amino]piperidine

Starting material: compound of Example XIV (1) $R_f$ value: 0.34 (silica gel, methylene chloride/methanol/concentrated aqueous ammonia=4:1:0.1).

(2) (R)-4-[N-(tert-butyloxycarbonylmethyl)-N-(2-hydroxypropyl)amino]piperidine

Starting material: Compound of Example XIV (2) Mass spectrum (ESI$^+$): m/z)−273 [M+H]$^+$.

(3) 4-hydroxy-4-[N-methyl-N-(ethoxycarbonylmethyl)aminomethyl]piperidine

Starting material: Compound of Example XVI $R_f$ value: 0.38 (silica gel, methylene chloride/methanol/concentrated aqueous ammonia=4:1:0.1).

EXAMPLE VII 3-(1-benzylpiperidin-4-ylidene)dihydrofuran-2-one 24.00 g of diethyl (2-oxotetrahydrofuran-3-yl)phosphonate is slowly added dropwise to 4.40 g of sodium hydride in 25 ml of toluene. 1-benzyl-9-piperidine-4-one is then added and the reaction mixture is refluxed for 3 hours. After cooling to ambient temperature, the supernatant solution is decanted off, diluted with toluene and washed with water and saturated sodium chloride solution. The organic phase is dried over magnesium sulfate, concentrated by evaporation, and chromatographed over a silica gel column with ethyl acetate/methanol (95:5) as eluant.

Yield: 14.43 g (52% of theory); $R_f$ value: 0.64 (silica gel, ethyl acetate/methanol=9:1); mass spectrum (ESI$^-$): m/z=256 [M−H]$^-$.

EXAMPLE VIII

4-[(3-chloro-4-fluorophenyl)amino]-6-({3-[1-(tert-butyloxycarbonyl)piperidin-4-yl]-1-oxo-2-propen-1-yl}amino)-7-cyclopropylmethoxyquinazoline 1.61 g of 4-[(3-chloro-4-fluorophenyl)amino]-6-({[(diethoxyphosphoryl)methyl]carbonyl}amino)-7- cyclopropylmethoxyquinazoline is added to 127 mg of anhydrous lithium chloride in 20 ml of absolute tetrahydrofuran under argon. The mixture is stirred for 15 minutes at ambient temperature, then cooled to 0° C. in an ice bath and 0.45 ml of 1,8-diazabicyclo[5.4.0]undec-7-ene is added. After another 30 minutes at 0° C., 690 mg of 4-formyl-1-(tert-butoxycarbonyl)piperidine is added. The reaction mixture is left overnight to come up to ambient temperature. For working up, the solvent is eliminated in vacuo and the residue in the flask is taken up with ethyl acetate/methanol (9:1). The solution is washed with water and saturated sodium chloride solution, dried over magnesium sulfate, and concentrated by evaporation. The oily, brown crude product is purified by chromatography through a silica gel column with ethyl acetate as eluant.

Yield: 1.30 g (73% of theory); $R_f$ value: 0.80 (silica gel, ethyl acetate); mass spectrum (EI): m/z=595, 597 [M]$^+$.

EXAMPLE IX

4-[(3-chloro-4-fluorophenyl)amino]-6-({[(diethoxyphosphoryl)methyl]carbonyl}amino)-7-cyclopropylmethoxyquinazoline 2.77 ml of triethylamine, 3.43 g of diethoxyphosphorylacetic acid, and 5.62 g of benzotriazol-1-yl-N-tetramethyluronium tetrafluoroborate are added successively to 5.00 g of 6-amino-4-[(3-chloro-4-fluorophenyl)amino]-7-cyclopropylmethoxyquinazoline in 25 ml of N,N-dimethylformamide. The reaction mixture is stirred for one hour at ambient temperature; 250 ml of water is then added and the mixture is extracted with 250 ml of ethyl acetate/methanol (10:1). The organic phase is washed with water and saturated sodium chloride solution, dried over magnesium sulfate, and concentrated by evaporation. The residue in the flask is crystallized by stirring with diethylether.

Yield: 7.00 g (94% of theory); melting point: 186° C.; mass spectrum (ESI-): m/z=535, 537 [M–H]$^-$.

EXAMPLE X 8-(tert-butyloxycarbonyl1perhydropyrazino[2,1-c][1,4]oxazin-3-one 2.00 g of 1-(tert-butyloxycarbonyl)-4-[(ethoxycarbonyl)methyl]-3-hydroxymethylpiperazine in 2.5 ml of acetonitrile is combined with 500 mg of p-toluenesulfonic acid monohydrate. The reaction mixture is refluxed for 3 hours until the reaction is complete; the solvent is then distilled off in vacuo. The crude product is further reacted without additional purification.

$R_f$ value: 0.80 (silica gel, ethyl acetate/methanol=9:1)

The following compound is obtained analogously to Example X:
(1) 8-(tert-butyloxycarbonyl)perhydropyrazino[2,1-c][1,4]oxazin-1-one $R_f$ value: 0.60 (silica gel, methylene chloride/methanol=95:5); mass spectrum (ESI$^+$): m/z=257 [M+H]$^+$.

EXAMPLE XI 1-(tert-butyloxcarbonyl)-4-[(ethoxycarbonyl)methyl]-3-hydroxymethylpiperazine and 8-(tert-butyloxycarbonyl)perhydropyrazino[2.1-c][1,4]oxazin-3-one 3.90 ml of ethyl bromoacetate is added to 5.80 g of 1-(tert-butyloxycarbonyl)-3-hydroxymethylpiperazine and 4.50 ml of triethylamine in 60 ml of acetonitrile. The reaction mixture is refluxed overnight, during which time two products are formed, according to thin layer chromatography. For working up, the reaction mixture is concentrated by evaporation in vacuo and the residue is divided between ethyl acetate and water. The organic phase is dried over magnesium sulfate, concentrated by evaporation, and chromatographed over a silica gel column with ethyl acetate/methanol (97:3). The following two products are obtained as yellowish oils:

8-(tert-butyloxycarbonyl)perhydropyrazino[2,1-c][1,4]oxazin-3-one

Yield: 3.43 g (50% of theory); $R_f$ value: 0.80 (silica gel, ethyl acetate/methanol=9:1).

1-(tert-butyloxycarbonyl)-4-[(ethoxycarbonyl)methyl]-3-hydroxymethylpiperazine

Yield: 2.08 g (26% of theory); $R_f$ value: 0.58 (silica gel, ethyl acetate/methanol=9:1); mass spectrum (ESI$^+$): m/z=303 [M+H]$^+$.

The following compounds are obtained analogously to Example XI:
(1) 8-(tert-butyloxycarbonyl)perhydropyrazino [2,1-c][1,4]oxazin-1-one $R_f$ value: 0.60 (silica gel, methylene chloride/methanol=95:5); mass spectrum (ESI$^+$): m/z=257 [M+H]$^+$.
(2) 1-(tert-butyloxycarbonyl)-3-(ethoxycarbonyl)-4-(2-hydroxyethyl)piperazine $R_f$ value: 0.50 (silica gel, methylene chloride/methanol=95:5); mass spectrum (EI): m/z=302 [M]$^+$.

EXAMPLE XII 1-(tert-butyloxycarbonyl)-3-hydroxymethylpiperazine

A solution of 8.00 g of 1-(tert-butyloxycarbonyl)-3-ethoxycarbonylpiperazine in 10 ml of tetrahydrofuran is added dropwise to a suspension of 900 mg of lithium borohydride in 20 ml of tetrahydrofuran and the mixture is then refluxed for 3 hours. For working up, the reaction mixture is concentrated by evaporation, adjusted to pH 4 with 10% aqueous citric acid solution, and stirred for about 40 minutes while cooling with an ice bath. The mixture is then made alkaline with concentrated sodium hydroxide solution and left to stand overnight. The next morning, it is extracted with tert-butylmethylether. The organic phase is dried over magnesium sulfate and concentrated by evaporation. A clear oil is left, which slowly crystallizes.

Yield: 5.80 g (87% of theory); $R_f$ value: 0.28 (silica gel, ethyl acetate/methanol=4:1); mass spectrum (ESI$^+$): m/z=217 [M+H]$^+$.

EXAMPLE XIII 1-(tert-butyloxycarbonyl)-3-ethoxycarbonylpiperazine 21.80 g of di-tert-butyl pyrocarbonate is added to 15.80 g of 2-ethoxycarbonylpiperazine in 400 ml of ethanol while cooling with an ice bath. The reaction mixture is stirred for another 3 hours at 0° C. It is then concentrated by evaporation and the residue is divided between ethyl acetate and water. The organic phase is dried over magnesium sulfate, concentrated by evaporation, and purified by chromatography through a silica gel column with ethyl acetate/methanol (95:5) as eluant.

Yield: 24.30 g (94% of theory); $R_f$ value: 0.40 (silica gel, ethyl acetate/methanol=9:1); mass spectrum (ESI$^+$): m/z=281 [M+Na]$^+$.

EXAMPLE XIV 1-tert-butyloxycarbonyl-4-methylaminopiperidine 25.50 g of methylamine hydrochloride is added to 15.00 g of 1-(tert-butyloxycarbonyl)-4-piperidinone and 31.20 g of sodium acetate in 300 ml of tetrahydrofuran. 19.00 g of sodium triacetoxyborohydride is then added batchwise. The reaction mixture is stirred overnight at ambient temperature and, the next day, concentrated by evaporation. The residue is divided between 5% sodium hydrogen carbonate solution and methylene chloride. The aqueous phase is adjusted to about pH 11 with 4N hydrochloric acid and extracted with ethyl acetate. The organic phase is dried over magnesium sulfate and concentrated by evaporation, leaving a colorless oil.

Yield: 12.74 g (79% of theory); $R_f$ value: 0.22 (silica gel, ethyl acetate/methanol/concentrated aqueous ammonia solution=90:10:1); mass spectrum (ESI$^+$): m/z=215 [M+H]$^+$.

The following compounds are obtained analogously to Example XIV:
(1) 1-benzyloxycarbonyl-4-[N-(tert-butyloxycarbonylmethyl)-N-(2-hydroxyethyl)amino]piperidine Mass spectrum (ESI$^+$): m/z=393 [M+H]$^+$; $R_f$ value: 0.50 (silica gel, cyclohexane/ethyl acetate=9:1).
(2) (R)-1-benzyloxycarbonyl-4-[N-(tert-butyloxycarbonylmethyl)-N-(2-hydroxypropyl)amino]piperidine Mass spectrum (ESI$^+$): m/z=407 [M+H]$^+$; $R_f$ value: 0.56 (silica gel, cyclohexane/ethyl acetate =9:1).

EXAMPLE XV 1-(tert-butyloxycarbonyl)-4-[(2-oxotetrahydrofuran-3-yl)sulfanyl]piperidine 2.73 g of potassium tert-butoxide is slowly added to 5.28 g of 1-(tert-butyloxycarbonyl)-4-mercaptopiperidine in 20 ml of N,N-dimethylformamide while cooling with an ice bath. The mixture is stirred for another 30 minutes while cooling with an ice bath, then a solution of 2.02 ml of 3-bromodihydrofuran-2-one in 20 ml of N,N-dimethylformamide is added dropwise. After the addition has finished, the reaction mixture is stirred for two hours at ambient temperature. It is then neutralized with glacial acetic acid and concentrated by evaporation. The residue is divided between ethyl acetate and water. The organic phase is dried over magnesium sulfate and concentrated by evaporation. 7.60 g of a brownish-orange oil remain, which is reacted without further purification.

$R_f$ value: 0.32 (silica gel, ethyl acetate/cyclohexane=2:3) mass spectrum (ESI$^-$): m/z=300 [M-H]$^-$

EXAMPLE XVI 1-benzyloxycarbonyl-4-hydroxy-4-[N-methyl-N-(ethoxycarbonylmethyl)aminomethyl]piperidine A mixture of 2.7 g of sarcosine ethyl ester and 3.09 g of 6-benzyloxycarbonyl-1-oxa-6-azaspiro[2.5]octane in 20 ml of ethanol is heated to 90° C. for 6 hours in a bomb tube. After cooling overnight, the mixture is evaporated down and the residue is purified by chromatography over a silica gel column with cyclohexane/ethyl acetate (1:1).

Yield: 1.8 g (25% of theory); mass spectrum (ESI$^+$): m/z=365 [M+H]$^+$; $R_f$ value: 0.35 (silica gel, cyclohexane/ethyl acetate=1:1).

Preparation of the Final Compounds

EXAMPLE 1

4-[(3-chloro-4-fluorophenyl)amino]-6-({4-[4-(2-oxotetrahydrofuran-3-yl)piperazin-1yl]-1-oxo-2-buten-1-yl}amino)-7-cyclopropylmethoxyquinazoline 0.42 ml of triethylamine is added to 608 mg of 4-[(3-chloro-4-fluorophenyl)amino]-6-{[4-(piperazin-1-yl)-1-oxo-2-buten-1-yl]amino}-7-cyclopropylmethoxyquinazoline in 3.0 ml of tetrahydrofuran. The mixture is cooled in the ice bath and a solution of 215 mg of 3-bromodihydrofuran-2-one in 1.0 ml of tetrahydrofuran is added dropwise and the mixture is stirred for one hour with cooling. The ice bath is then removed and the mixture is stirred for about 48 hours at ambient temperature. The reaction mixture is chromatographed directly, without further processing, over a silica gel column, with methylene chloride/methanol (95:5 to 90:10) as eluant. The foamy crude product is crystallized by trituration with a little diethylether.

Yield: 393 mg (56% of theory); melting point: 130-131° C.; mass spectrum (ESI$^-$): m/z=593, 595 [M-H]$^-$.

The following compounds are obtained analogously to Example 1:
(1) (R)-4-[(3-chloro-4-fluorophenyl)amino]-6-[(4-{4-[(5-oxotetrahydrofuran-2-yl)methyl]piperazin-1-yl}-1-oxo-2-buten-1-yl)amino]-7-cyclopropylmethoxyquinazoline (The reaction is carried out with (R)-5-mesyloxymethyl-2-oxotetrahydrofuran without a solvent). Melting point: 145° C.–150° C.; mass spectrum (ESI$^-$): m/z=607, 609 [M-H]$^-$.
(2) 4-[(3-chloro-4-fluorophenyl)amino]-6-[(4-{4-[N-(2-oxotetrahydrofuran-3-yl)-N-methylamino]piperidin-1-yl}-1-oxo-2-buten-1-yl)amino]-7-cyclopropylmethoxyquinazoline $R_f$ value: 0.22 (silica gel, ethyl acetate/methanol=7:3); mass spectrum (ESI$^-$): m/z=621, 623 [M-H]$^-$.
(3) 4-[(3-chloro-4-fluorophenyl)amino]-6-[(4-{N-[1-(2-oxotetrahydrofuran-3-yl)piperiden-4-yl]-N-methylamino}-1-oxo-2-buten-1-yl)amino]-7-cyclopropylmethoxyquinazoline $R_f$ value: 0.73 (aluminium oxide, ethyl acetate/methanol= 9:1); mass spectrum (ESI$^-$): m/z=621, 623 [M-H]$^-$.

EXAMPLE 2

4-[(3-chloro-4-fluorophenyl)amino]-6-({4-[4-(2-oxotetrahydrofuran-4-yl)piperazin-1-yl]-1-oxo-2-buten-1-yl}amino)-7-cyclopropylmethoxyquinazoline 78 µl of 2(5H)-furanone is added to 500 mg of 4-[(3-chloro-4-fluorophenyl)amino]-6-{[4-(piperazin-1-yl)-1-oxo-2-buten-1-yl]amino}-7-cyclopropylmethoxyquinazoline in 2 ml of methanol. The reaction mixture is stirred for about 48 hours at ambient temperature and then evaporated to dryness in vacuo. The residue in the flask is purified by chromatography through a silica gel column with methylene chloride/methanol (95:5 to 90:10) as eluant. The product obtained is recrystallized from ethyl acetate.

Yield: 170 mg (29% of theory); $R_f$ value: 0.43 (silica gel, methylene chloride/methanol=9:1); mass spectrum (ESI$^-$): m/z=593, 595 [M–H]$^-$.

The following compound is obtained analogously to Example 2:
(1) 4-[(3-chloro-4-fluorophenyl)amino]-6-({3-[1-(2-oxotetrahydrofuran-4-yl)piperidin-4-yl-1-oxo-2propen-1-yl}amino)-7-cyclopropylmethoxyquinazoline Melting point: 138° C.; mass spectrum (ESI$^-$): m/z=578, 580 [M–H]$^-$.

EXAMPLE 3

(S)-4-[(3-chloro-4-fluorophenyl)amino]-6-[(4-{4-[(5-oxotetrahydrofuran-2-yl)carbonyl]piperazin-1-yl}-1-oxo-2-buten-1-yl)amino]-7-cyclopropylmethoxyquinazoline 130 mg of (S)-5-oxotetrahydrofuran-2-carboxylic acid, 0.21 ml of triethylamine, and 321 mg of benzotriazol-1-yl-N-tetramethyluronium tetrafluoroborate are added to 500 mg of 4-[(3-chloro-4-fluorophenyl)amino]-6-{[4-(piperazin-1-yl)-1-oxo-2-buten-1-yl]amino}-7-cyclopropylmethoxyquinazoline in 3 ml of N,N-dimethylformamide. The reaction mixture is left to stand for about 48 hours at ambient temperature; 20 ml of water is then added, whereupon a greasy precipitate is formed. This is suction filtered, washed with water and purified by chromatography through a silica gel column with methylene chloride/methanol (95:5 to 90:10) as eluant.

Yield: 330 mg (54% of theory); melting point: 155° C.–157° C.; mass spectrum (ESI$^-$): m/z=621, 623 [M–H]$^-$.

The following compound is obtained analogously to Example 3:
(1) 4-[(3-Chloro-4-fluorophenyl)amino]-6-{[4-(N-{1-[((S)-5-oxotetrahydrofuran-2-yl)carbonyl]piperidin-4-yl}-N-methylamino)-1-oxo-2-buten-1-yl]amino}-7-cyclopropylmethoxyquinazoline $R_f$ value: 0.36 (silica gel, ethyl acetate/methanol/concentrated aqueous ammonia solution=9:1:0.2); mass spectrum (EI): m/z=650, 652 [M]$^+$.

EXAMPLE 4

4-[(3-chloro-4-fluorophenyl)amino]-6-{[4-(4-{2-[(2-oxotetrahydrofuran-3-yl)sulfanyl]ethyl}piperazin-1-yl)-1-oxo-2-buten-1-yl]amino}-7-cyclopropylmethoxyquinazoline 0.67 ml of oxalyl chloride is added dropwise at ambient temperature to a solution of 644 mg g of 4-bromocrotonic acid in 15 ml of methylene chloride. After the addition of one drop of N,N-dimethylformamide, the reaction mixture is stirred for about another hour at ambient temperature, until the development of gas has ceased. The solvent is then distilled off in vacuo from the acid chloride formed. In the meantime, 1.00 g of 6-amino-4-[(3-chloro-4-fluorophenyl)amino]-7-cyclopropylmethoxyquinazoline and 8.0 ml of diisopropylethylamine in 30 ml of tetrahydrofuran are cooled to 0° C. in an ice bath. The crude acid chloride is taken up in 10 ml of methylene chloride and added dropwise within 5 minutes while cooling with an ice bath. The reaction mixture is stirred for another hour at 0° C. and for two hours at ambient temperature. A suspension of 4.35 N-{2-[(2-oxotetrahydrofuran-3-yl)sulfanyl]ethyl}piperazine in 5 ml of methylene chloride is then added and the whole is stirred for another 48 hours at ambient temperature. The reaction mixture is concentrated by evaporation in vacuo and the residue in the flask is chromatographed through a silica gel column with ethyl acetate/methanol (95:5 to 90: 10) as eluant.

Yield: 20 mg (1% of theory); $R_f$ value: 0.32 (silica gel, methylene chloride/methanol=9:1); mass spectrum (ESI$^-$): m/z=653, 655 [M–H]$^-$.

The following compounds are obtained analogously to Example 4:
(1) 4-[(3-chloro-4-fluorophenyl)amino]-6-({4-[4-(2-oxotetrahydrofuran-3-yl)piperidin-1-yl]-1-oxo-2buten-1-yl}amino)-7-cyclopropylmethoxyquinazoline $R_f$ value: 0.17 (silica gel, ethyl acetate/methanol=9:1); mass spectrum (ESI$^-$): m/z=592, 594 [M–H]$^-$.

(2) 4-[(3-chloro-4-fluorophenyl)amino]-6-{[4-(3-oxo-2-oxa-8-azaspiro[4.5]dec-8-yl)-1-oxo-2-buten-1-yl]amino}-7-cyclopropylmethoxyquinazoline (The 2-oxa-8-azaspiro[4.5]decan-3-one used is obtained from 8-benzyl-2-oxa-8-azaspiro[4.5]decan-3-one by hydrogenolytic cleaving of the benzyl group). $R_f$ value: 0.37 (silica gel, methylene chloride/methanol=9:1); mass spectrum (EI): m/z=579, 581 [M]$^+$.

(3) 4-[(3-chloro-4-fluorophenyl)amino]-6-{[4-(3-oxoperhydropyrazino[2,1-c][1,4]oxazin-8-yl)-1-oxo-2-buten-1-yl]amino}-7-cyclopropylmethoxyquinazoline $R_f$ value: 0.19 (silica gel, ethyl acetate/methanol=9:1); mass spectrum (ESI$^-$): m/z=579, 581 [M–H]$^-$.

(4) 4-[(3-chloro-4-fluorophenyl)amino]-6-{[4-(1-oxo-2-oxa-8-azaspiro[4.5]dec-8-yl)-1-oxo-2-buten-1-yl]amino}-7-cyclopropylmethoxyquinazoline $R_f$ value: 0.48 (silica gel, methylene chloride/methanol= 9:1); mass spectrum (EI): m/z=579, 581 [M]$^+$.

(5) 4-[(3-chloro-4-fluorophenyl)amino]-6-{[4-(1-oxoperhydropyrazino[2,1-c][1,4]oxazin-8-yl)-1-oxo-2-buten-1-yl]amino}-7-cyclopropylmethoxyquinazoline $R_f$ value: 0.21 (silica gel, ethyl acetate/methanol=9:1); mass spectrum (ESI$^-$): m/z=579, 581 [M–H]$^-$.

(6) 4-[(3-chloro-4-fluorophenyl)amino]-6-[(4-{4-[(2-oxotetrahydrofuran-3yl)sulfany]piperidin-1-yl}-1-oxo-2-buten-1-yl)amino]-7-cyclopropylmethoxyquinazoline $R_f$ value: 0.23 (silica gel, ethyl acetate/methanol=9:1); mass spectrum (ESI$^-$): m/z=624, 626 [M–H]$^-$.

(7) 4-[(3-chloro-4-fluorophenyl)amino]-6-[(4-{4-[(2-oxo-6,6-dimethylmorphol 4-yl)methyl]piperidin-1-y}-1-oxo-2-buten-1-yl)amino]-7-cyclopropylmethoxyquinazoline $R_f$ value: 0.48 (silica gel, ethyl acetate/methanol/concentrated aqueous ammonia=9:1:0.2) mass spectrum (ESI$^-$): m/z=649, 651 [M–H]$^-$.

(8) 4-((3-chloro-4-fluorophenyl)amino)-6-({4-[4-(2-oxomorpholin-4-yl)piperidin-1yl]-1-oxo-2buten-1-yl}amino)-7-cyclopropylmethoxyquinazoline Prepared by lactonizing the intermediate product (4-[(3-chloro-4-fluorophenyl)amino]-6-({4-[4-[N-(tert-butyloxycarbonylmethyl)-N-(2-hydroxyethyl)amino]piperidin-1-yl]-1-oxo-2-buten-1-yl}amino)-7-cyclopropylmethoxyquinazoline, melting point 114–117° C. (with foaming), $R_f$ value: 0.46 (silica gel, methylene chloride/methanol=9:1)) in the presence of 5 equivalents of trifluoroacetic acid in acetonitrile under reflux.

Melting point: from 140° C. (with foaming); mass spectrum (ESI$^+$): m/z=609, 611 [M+H]$^+$; $R_f$ value: 0.26 (silica gel, ethyl acetate/methanol=4:1).

(9) (R)-4-[(3-chloro-4-fluorophenyl)amino]-6-({4-[4-(6-methyl-2-oxomorpholin-4yl)piperidin-1yl]-1-oxo-2buten-1yl}amino)-7-cyclopropylmethoxyquinazoline Prepared by lactonizing the intermediate product ((R)-4-[(3-chloro-4-fluorophenyl)amino]-6 ({4-[4-[N-(tert-butyloxycarbonylmethyl)-N-(2-hydroxypropyl)amino]

piperidin-1-yl]-1-oxo-2-buten-1-yl}amino)-7-cyclopropylmethoxyquinazoline, melting point: from 115° C. (with foaming); R$_f$ value: 0.53 (silica gel, methylene chloride/methanol 9:1)) in the presence of 5 equivalents of trifluoroacetic acid in acetonitrile under reflux; melting point: from 126° C. (with foaming); mass spectrum (ESI$^+$): m/z=623, 625 [M+H]$^+$; R$_f$ value: 0.29 (silica gel, ethyl acetate/methanol 4:1).

(10) 4-[(3-chloro-4-fluorophenyl)amino]-6-([4-(4-methyl-2-oxo-1-oxa-4,9-diazaspiro 5.5]undec-9-yl)-1-oxo-2-buten-1-yl]amino}-7-cyclopropylmethoxyquinazoline Melting point: 125–130° C. (with foaming); mass spectrum (ESI$^+$): m/z=609, 611 [M+H]$^+$; R$_f$ value: 0.46 (silica gel, methylene chloride/methanol=9:1)

(11) 4-[(3-chloro-4-fluorophenyl)amino]-6-{[4-(2-oxo-3-oxa-9-azaspiro[5.5]undec-9-yl)-1-oxo-2-buten-1-yl]amino}-7-cyclopropylmethoxyquinazoline Mass spectrum (ESI$^-$): m/z=592, 594 [M+H]$^-$; R$_f$ value: 0.24 (silica gel, methylene chloride/methanol 9:1).

The starting material 2-oxo-3-oxa-9-azaspiro[5.5] undecane is prepared as follows:

(a) 4,4-bis-(2-hydroxyethyl)piperidine is prepared by catalytic hydrogenation of 1-benzyl-4,4-bis-(2-hydroxyethyl)piperidine in ethanol in the presence of palladium on activated carbon (10% Pd).

Mass spectrum (ESI$^+$): m/z=174 [M+H]$^+$.

(b) 1-benzyloxycarbonyl-4,4-bis-(2-hydroxyethyl)piperidine is prepared by reaction of 4,4-bis-(2-hydroxyethyl)piperidine with benzyl chloroformate in tetrahydrofuran in the presence of triethylamine.

R$_f$ value: 0.32 (silica gel, ethyl acetate/methanol=9:1).

(c) 9-benzyloxycarbonyl-2-oxo-3-oxa-9-azaspiro[5.5] undecane is prepared by reaction of 1-benzyloxycarbonyl-4,4-bis-(2-hydroxyethyl)piperidine with 4-methylmorpholine-N-oxide in methylene chloride/acetonitrile in the presence of tetrapropylammonium perruthenate and pulverized molecular sieve.

mass spectrum (ESI$^-$): m/z 302 [M+H]$^-$.

(d) 2-oxo-3-oxa-9-azaspiro[5.5]undecane is prepared by catalytic hydrogenation of 9-benzyloxycarbonyl-2-oxo-3-oxa-9-azaspiro[5.5]undecane in ethanol in the presence of palladium on activated carbon (10% Pd) (the product must be reacted further immediately after careful evaporation). Mass spectrum (ESI$^+$): m/z 170 [M+H]$^+$.

The following compounds may also be obtained analogously to the preceding Examples and other methods known from the literature:

(1) 4-[(3-chloro-4-fluorophenyl)amino]-6-{[4-(7-oxo-6-oxa-2,9-diazaspiro[4.5]dec-2-yl)-1-oxo-2-buten-1-yl]amino}-7-cyclopropylmethoxyquinazoline (2) 4-[(3-chloro-4-fluorophenyl)amino]-6-{[4-(7-oxo-6,9-dioxa-2-azaspiro[4.5]dec-2-yl)-1-oxo-2-buten-1-yl]amino}-7-cyclopropylmethoxyquinazoline (3) 4-[(3-chloro-4-fluorophenyl)amino]-6-{[4-(3-oxo-2-oxa-7-azaspiro[4.4]non-7-yl)-1-oxo-2-buten-1-yl]amino}-7-cyclopropylmethoxyquinazoline (4) 4-[(3-chloro-4-fluorophenyl)amino]-6-{[4-(2-oxo-1,4-dioxa-9-azaspiro[5.5]undec-9-yl)-1-oxo-2-buten-1-yl]amino}-7-cyclopropylmethoxyquinazoline (5) 4-[(3-chloro-4-fluorophenyl)amino]-6-{[4-(2-oxo-4-methyl-1-oxa-4,9-diazaspiro[5.5]undec-9-yl)-1-oxo-2-buten-1-yl]amino}-7-cyclopropylmethoxyquinazoline (6) 4-[(3-chloro-4-fluorophenyl)amino]-6-{[4-(2-oxo-1-oxa-9-azaspiro[5.5]undec-9-yl)-1-oxo-2-buten-1-yl]amino}-7-cyclopropylmethoxyquinazoline (7) 4-[(3-chloro-4-fluorophenyl)amino]-6-{[4-(3-oxo-1,4-dioxa-9-azaspiro[5.5]undec-9-yl)-1-oxo-2-buten-1-yl]amino}-7-cyclopropylmethoxyquinazoline (8) 4-[(3-chloro-4-fluorophenyl)amino]-6-{[4-(4-oxoperhydrofuro[3,4-b]pyrrol-1-yl)-1-oxo-2-buten-1-yl]amino}-7-cyclopropylmethoxyquinazoline (9) 4-[(3-chloro-4-fluorophenyl)amino]-6-{[4-(6-oxoperhydrofuro[3,4-b]pyrrol-1-yl)-1-oxo-2-buten-1-yl]amino}-7-cyclopropylmethoxyquinazoline

(10) 4-[(3-chloro-4-fluorophenyl)amino]-6-{[4-(2-oxoperhydrofuro[2,3-c]pyrrol-5-yl)-1-oxo-2-buten-1-yl]amino}-7-cyclopropylmethoxyquinazoline

(11) 4-[(3-chloro-4-fluorophenyl)amino]-6-{[4-(2-oxo-4-methylperhydropyrrolo-[3,4-b][1.4]oxazin-6-yl)-1-oxo-2-buten-1-yl]amino}-7-cyclopropylmethoxyquinazoline

(12) 4-[(3-chloro-4-fluorophenyl)amino]-6-{[4-(2-oxoperhydro-[1.4]dioxino[2,3-c]pyrrol-6-yl)-1-oxo-2-buten-1-yl]amino}-7-cyclopropylmethoxyquinazoline

(13) 4-[(3-chloro-4-fluorophenyl)amino]-6-({4-[4-(2-oxotetrahydrofuran-4-yl)piperidin-1-yl]-1-oxo-2-buten-1-yl}amino)-7-cyclopropylmethoxyquinazoline

(14) 4-[(3-chloro-4-fluorophenyl)amino]-6-({4-[4-(2-oxo-4-methylmorpholin-3-yl)piperidin-1-yl]-1-oxo-2-buten-1-yl}amino)-7-cyclopropylmethoxyquinazoline

(15) 4-[(3-chloro-4-fluorophenyl)amino]-6-({4-[4-(2-oxo-4-methylmorpholin-6-yl)piperidin-1-yl]-11-oxo-2-buten-1-yl}amino)-7-cyclopropylmethoxyquinazoline

(16) 4-[(3-chloro-4-fluorophenyl)amino]-6-({4-[3-(2-oxo-6,6-dimethylmorpholin-4-yl)pyrrolidin-1-yl]-1-oxo-2-buten-1-yl}amino)-7-cyclopropylmethoxyquinazoline

(17) 4-[(3-chloro-4-fluorophenyl)amino]-6-({4-[4-(2-oxo-6,6-dimethylmorpholin-4-yl)piperidin-1-yl]-1-oxo-2-buten-1-yl}amino)-7-cyclopropylmethoxyquinazoline

(18) 4-[(3-chloro-4-fluorophenyl)amino]-6-[(4-{4-[(2-oxotetrahydrofuran-3-yl)oxy]piperidin-1-yl}-1-oxo-2-buten-1-yl)amino]-7-cyclopropylmethoxyquinazoline

(19) 4-[(3-chloro-4-fluoropheny)amino]-6-{[4-(4-{2-[(2-oxotetrahydrofuran-3yl)oxy]ethyl}piperazin-1-yl)-1-oxo-2-buten-1-yl]amino}-7-cyclopropylmethoxyquinazoline

(20) 4-[(3-chloro-4-fluorophenyl)amino]-6-{[4-(4-{[(2-oxotetrahydrofuran-3-yl)oxy]acetyl}piperazin-1-yl)-1-oxo-2-buten-1-yl]amino}-7-cyclopropylmethoxyquinazoline

(21) 4-[(3-chloro-4-fluorophenyl)amino]-6-{[4-(4-{[(2-oxotetrahydrofuran-3-yl)sulfanyl]acetyl}piperazin-1-yl)-1-oxo-2-buten-1-yl]amino}-7cyclopropylmethoxyquinazoline

(22) 4-[(3-chloro-4-fluorophenyl)amino]-6-[(4-{2-[2-(2-oxo-6,6-dimethylmorpholin-4-yl)ethyl]piperazin-1-yl}-1-oxo-2-buten-1-yl)amino]-7-cyclopropylmethoxyquinazoline

(23) 4-[(3-chloro-4-fluorophenyl)amino]-6-[(4-{4-[(2-oxo-6,6-dimethylmorpholin-4-yl)acetyl]piperazin-1-yl}-1-oxo-2-buten-1-yl)amino]-7-cyclopropylmethoxyquinazoline

(24) 4-[(3-chloro-4-fluorophenyl)amino]-6-[(4-{4-[(2-oxo-6,6-dimethylmorpholin-4-yl)methyl]-piperidin-1-yl}-1-oxo-2-buten-1-yl)amino]-7-cyclopropylmethoxyquinazoline

(25) 4-[(3-chloro-4-fluorophenyl)amino]-6-{[4-(N-{1-[(5-oxotetrahydrofuran-2-yl)carbonyl]piperidin-4-yl}-N-methylamino)-1-oxo-2-buten-1-yl]amino}-7-cyclopropyl-methoxyquinazoline

(26) 4-[(3-chloro-4-fluorophenyl)amino]-6-[(4-{4-[(5-oxotetrahydrofuran-2-yl)carbonylamino]piperidin-1-yl}-1-oxo-2-buten-1-yl)amino]-7-cyclopropylmethoxyquinazoline

(27) 4-[(3-chloro-4-fluorophenyl)amino]-6-{[4-(4-{N -[(5-oxotetrahydrofuran-2yl)carbonyl]-N-methylamino}piperidin-1-yl)-1-oxo-2-buten-1-yl]amino}-7-cyclopropyl-methoxyquinazoline

(28) 4-[(3-chloro-4-fluorophenyl)amino]-6-{[4-(3-oxoperhydropyrazino-[2,1-c][1,4]oxazin-8-yl)-1-oxo-2-buten-1-yl]amino}-7-cyclobutylmethoxyquinazoline
(29) 4-[(3-chloro-4-fluorophenyl)amino]-6-{[4-(3-oxoperhydropyrazino-[2,1-c][1,4]oxazin-8-yl)-1-oxo-2-buten-1-yl]amino}-7-cyclobutyloxyquinazoline
(30) 4-[(3-chloro-4-fluorophenyl)amino]-6-{[4-(3-oxoperhydropyrazino-[2,1-c][1,4]oxazin-8-yl)-1-oxo-2-buten-1-yl]amino}-7-cyclopentyloxyquinazoline
(31) 4-[(3-chloro-4-fluorophenyl)amino]-6-{[4-(3-oxoperhydropyrazino-[2,1-c][1,4]oxazin-8-yl)-1-oxo-2-buten-1-yl]amino}-7-[(tetrahydrofuran-3-yl)oxy]quinazoline
(32) 4-[(3-chloro-4-fluorophenyl)amino]-6-{[4-(3-oxoperhydropyrazino-[2,1-c][1,4]oxazin-8-yl)-1-oxo-2-buten-1-yl]amino}-7-cyclohexyloxyquinazoline
(33) 4-[(3-chloro-4-fluorophenyl)amino]-6-{[4-(3-oxoperhydropyrazino-[2,1-c][1,4]oxazin-8-yl)-1-oxo-2-buten-1-yl]amino}-7-[(tetrahydropyran-4-yl)oxy]quinazoline
(34) 4-[(3-chloro-4-fluorophenyl)amino]-6-{[4-(3-oxoperhydropyrazino-[2,1-c][1,4]oxazin-8-yl)-1-oxo-2-buten-1-yl]amino}-7-[2-(cyclobutyloxy)ethoxy]quinazoline
(35) 4-[(3-chloro-4-fluorophenyl)amino]-6-{[4-(3-oxoperhydropyrazino-[2,1c][1,4]oxazin-8-yl)-1-oxo-2-buten-1-yl]amino}-7-[2-(cyclopropylmethoxy)ethoxy]quinazoline
(36) (R)-4-[(1-phenylethyl)amino]-6-{[4-(3-oxoperhydropyrazino[2,1-c][1,4]oxazin-8yl)-1-oxo-2-buten-1-yl]amino}quinazoline
(37) (R)-4-[(1-Phenylethyl)amino]-6-{[4-(3-oxoperhydropyrazino[2,1-c][1,4]oxazin-8-yl)-1-oxo-2-buten-1-yl]amino}-7-methoxyquinazoline
(38) (R)-4-[(1-phenylethyl)amino]-6-{[4-(3-oxoperhydropyrazino[2,1-c][1,4]oxazin-8-yl)-1-oxo-2-buten-1-yl]amino}-7-ethoxyquinazoline
(39) (R)-4-[(1-phenylethyl)amino]-6-{[4-(3-oxoperhydropyrazino[2,1-c][1,4]oxazin-8-yl)-1-oxo-2-buten-1-yl]amino}-7-[2-(methoxy)ethoxy]quinazoline
(40) (R)-4-[(1-phenylethyl)amino]-6-{[4-(3-oxoperhydropyrazino[2,1-c][1,4]oxazin-8-yl)-1-oxo-2-buten-1-yl]amino}-7-[3-(methoxy)propyloxy]quinazoline
(41) 4-[(3-chloro-4-fluorophenyl)amino]-6-({4-[4-(2-oxomorpholin-4-yl)piperidin-1-yl]-1-oxo-2-buten-1-yl}amino)-7-methoxyquinazoline
(42) 4-[(3-chloro-4-fluorophenyl)amino]-6-({4-[4-(2-oxomorpholin-4-yl)piperidin-1-yl]-1-oxo-2-buten-1-yl}amino-7-cyclopropylmethoxyquinazoline
(43) 4-[(R)-(1-phenylethyl)amino]-6-({4-[4-(2-oxomorpholin-4-yl)piperidin-1-yl]-1-oxo-2buten-1-yl}amino)quinazoline
(44) 4-[(3-chloro-4-fluorophenyl)amino]-6-({4-[4-(6-methyl-2-oxomorpholin-4-yl)piperidin-1-yl]-1-oxo-2buten-1-yl}amino-7-methoxyquinazoline
(45) 4-[(3-chloro-4-fluorophenyl)amino]-6-({4-[4-(6-methyl-2-oxomorpholin-4-yl)piperidin-1-yl]-1-oxo-2buten-1-yl}amino-7cyclopropylmethoxyquinazoline
(46) 4-[(R)-(1-phenylethyl)amino)-6-({4-[4-(6-methyl-2-oxomorpholin-4-yl)piperidin-1-yl]-1-oxo-2-buten-1-yl}amino)quinazoline
(47) 4-[(3-chloro-4-fluorophenyl)amino]-6-{[4-(2-oxo-3-oxa-9-azaspiro[5.5]undec-9-yl)-1-oxo-2-buten-1-yl]amino}-7-methoxyquinazoline
(48) 4-[(3-chloro-4-fluorophenyl)amino]-6-{[4-(2-oxo-3-oxa-9-azaspiro[5.5]undec-9-yl)-1-oxo-2-buten-1-yl]amino}-7-cyclopropylmethoxyquinazoline
(49) 4-[(R)-(1-phenylethyl)amino]-6-{[4-(2-oxo-3-oxo-9-azaspiro[5.5]undec-9-yl)-1-oxo-2-buten-1-yl]amino}quinazoline
(50) 4-[(3-chloro-4-fluorophenyl)amino]-6-{[4-(4-methyl-2-oxo-1-oxa-4,9diazaspiro[5.5]undec-9-yl)-1-oxo-2-buten-1-yl]amino}-7-methoxyquinazoline
(51) 4-[(R)-(1-Phenylethyl)amino]-6-{[4-(4-methyl-2-oxo-1-oxa-4,9-diazaspiro[5.5]undec-9-yl)-1-oxo-2-buten-1-yl]amino}quinazoline
(52) 4-[(3-chloro-4-fluorophenyl)amino]-6-[(4-{4-[(2-oxotetrahydrofuran-3-yl)sulfanyl]piperidin-1-yl}-1-oxo-2-buten-1-yl)amino]-7-[(tetrahydrofuran-2-yl)methoxy]quinazoline
(53) 4-[(3-chloro-4-fluorophenyl)amino]-6-[(4-{4-[(2-oxotetrahydrofuran-3-yl)sulfanyl]piperidin-1-yl}-oxo-2-buten-1-yl)amino]-7[-(tetrahydropyran-4-yl)methoxy]quinazoline

EXAMPLE 5

Coated Tablets Containing 75 mg of Active Substance

1 Tablet Core Contains

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape. Weight of core: 230 mg; die: 9 mm, convex. The tablet cores thus produced are coated with a film consisting essentially of hydroxypropylmethylcellulose. The finished film-coated tablets are polished with beeswax. Weight of coated tablet: 245 mg.

EXAMPLE 6

Tablets Containing 100 mg of Active Substance

Composition

1 Tablet Contains

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Preparation

The active substance, lactose and starch are mixed together and uniformly moistened with an aqueous solution of the polyvinylpyrrolidone. After the moist composition has been screened (2.0 mm mesh size) and dried in a rack-type drier at 50° C., it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 7

Tablets Containing 150 mg of Active Substance

Composition

1 Tablet Contains

| active substance | 50.0 mg |
|---|---|
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE 8

Hard Gelatine Capsules Containing 150 mg of Active Substance

1 Capsule Contains

| active substance | 50.0 mg |
|---|---|
| corn starch (dried) | approx. 80.0 mg |
| lactose (powdered) | approx. 87.0 mg |
| magnesium stearate | 3.0 mg |
| | approx. 420.0 mg |

Preparation

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 9

Suppositories Containing 150 mg of Active Substance

1 Suppository Contains

| active substance | 150.0 mg |
|---|---|
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation

After the suppository mass has been melted, the active substance is homogeneously distributed therein and the melt is poured into chilled molds.

EXAMPLE 10

Suspension Containing 50 mg of Active Substance

Composition 100 ml of Suspension Contains

| active substance | 1.00 g |
|---|---|
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavoring | 0.30 g |
| dist. water | ad 100 ml |

Preparation

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution, and the flavoring have been added and dissolved, the suspension is evacuated with stirring to eliminate air. 5 ml of suspension contains 50 mg of active substance.

EXAMPLE 11

Ampoules Containing 10 mg Active Substance

Composition

| active substance | 10.0 mg |
|---|---|
| 0.01N hydrochloric acid | q.s. |
| double-distilled water | ad 2.0 ml |

Preparation

The active substance is dissolved in the necessary amount of 0.01N HCl, made isotonic with common salt, filtered sterile and transferred into 2 ml ampoules.

EXAMPLE 12

Ampoules Containing 50 mg of Active Substance

Composition

| active substance | 50.0 mg |
|---|---|
| 0.01N hydrochloric acid | q.s. |
| double-distilled water | ad 10.0 ml |

Preparation

The active substance is dissolved in the necessary amount of 0.01N HCl, made isotonic with common salt, filtered sterile and transferred into 10 ml ampoules.

EXAMPLE 13

Capsules for Powder Inhalation Containing 5 mg of Active Substance

1 Capsule Contains

| active substance | 5.0 mg |
|---|---|
| lactose for inhalation | 15.0 mg |
| | 20.0 mg |

Preparation

The active substance is mixed with lactose for inhalation. The mixture is packed into capsules in a capsule-making machine (weight of the empty capsule approx. 50 mg).

weight of capsule: 70.0 mg size of capsule: 3

EXAMPLE 14

Solution for Inhalation for Hand-held Nebulisers Containing 2.5 mg Active Substance 1 Spray Contains

EXAMPLE 14

| Solution for inhalation for hand-held nebulisers containing 2.5 mg active substance | |
|---|---|
| 1 spray contains: | |
| active substance | 2.500 mg |
| benzalkonium chloride | 0.001 mg |
| 1N hydrochloric acid | q.s. |
| ethanol/water (50/50) | ad 15.000 mg |

Preparation

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g.

What is claimed is:
1. A compound of formula (I):

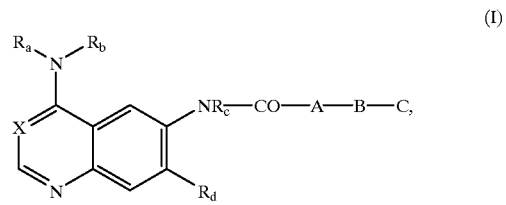

wherein:
X is a nitrogen atom;
$R_a$ is a hydrogen atom or a $C_{1-4}$-alkyl group;
$R_b$ is a phenyl, benzyl, or 1-phenylethyl group, wherein the phenyl nucleus in each case is substituted by the groups $R_1$ to $R_3$, wherein
$R_1$ and $R_2$, which are identical or different, are each
a hydrogen, fluorine, chlorine, bromine, or iodine atom,
a $C_{1-4}$-alkyl, hydroxy, $C_{1-4}$-alkoxy, $C_{3-6}$-cycloalkyl, $C_{4-6}$-cycloalkoxy, $C_{2-5}$-alkeny, or $C_{2-5}$-alkynyl group,
an aryl, aryloxy, arylmethyl, or arylmethoxy group,
a $C_{3-5}$-alkenyloxy or $C_{3-5}$-alkynyloxy group, wherein the unsaturated moiety is not linked to the oxygen atom,
a $C_{1-4}$-alkylsulfenyl, $C_{1-4}$-alkylsulfinyl, $C_{1-4}$-alkylsulfonyl, $C_{1-4}$-alkylsulfonyloxy, trifluoromethylsulfenyl, trifluoromethylsulfinyl, or trifluoromethylsulfonyl group,
a methyl or methoxy group substituted by 1 to 3 fluorine atoms,
an ethyl or ethoxy group substituted by 1 to 5 fluorine atoms,
a cyano or nitro group or an amino group optionally substituted by one or two $C_{1-4}$-alkyl groups, wherein the substituents are identical or different, or
$R_1$ together with $R_2$, if they are bound to adjacent carbon atoms, are a —CH=CH—CH=CH—, —CH=CH—NH—, or —CH=N—NH— group, and
$R_3$ is a hydrogen, fluorine, chlorine, or bromine atom, or a $C_{1-4}$-alkyl, trifluoromethyl, or $C_{1-4}$-alkoxy group;
$R_c$ is a hydrogen atom or a $C_{1-4}$-alkyl group;
$R_d$ is a hydrogen atom, or a $C_{1-6}$-alkoxy, $C_{4-7}$-cycloalkoxy, or $C_{3-7}$-cycloalkyl-$C_{1-4}$-alkoxy group,
a $C_{2-6}$-alkoxy group substituted from position 2 by a hydroxy, $C_{1-4}$-alkoxy, $C_{4-7}$-cycloalkoxy, $C_{3-7}$-cycloalkyl-$C_{1-3}$-alkoxy, di-($C_{1-4}$-alkyl)-amino, pyrrolidino, piperidino, morpholino, piperazino, or 4-($C_{1-4}$-alkyl)piperazino group, wherein the cyclic imino groups thereof are optionally substituted by one or two $C_{1-2}$-alkyl groups, or
a tetrahydrofuran-3-yloxy, tetrahydropyran-3-yloxy, tetrahydropyran-4-yloxy, tetrahydrofuranylmethoxy, or tetrahydropyranylmethoxy group;
A is a 1,1- or 1,2-vinylene group optionally substituted by a methyl or trifluoromethyl group or by two methyl groups, or
a 1,3-butadien-1,4-ylene group optionally substituted by a methyl or trifluoromethyl group or by two methyl groups, or an ethynylene group;

B is a $C_{1-6}$-alkylene group wherein one or two hydrogen atoms are optionally replaced by fluorine atoms, or, if B is bound to a carbon atom of C, it is optionally a bond; and C is a pyrrolidino group wherein the two hydrogen atoms in the 2 position are replaced by D, a pyrrolidino group wherein the two hydrogen atoms in the 3 position are replaced by E, a piperidino or hexahydroazepino group wherein the two hydrogen atoms in the 2 position are replaced by D, a piperidino or hexahydroazepino group wherein the two hydrogen atoms in the 3 position or in the 4 position are replaced by E, a piperazino or 4-($C_{1-4}$-alkyl)piperazino group wherein the two hydrogen atoms in the 2 position or in the 3 position of the piperazino ring are replaced by D, a pyrrolidino or piperidino group wherein two vicinal hydrogen atoms are replaced by an —O—CO—$CH_2$—, —$CH_2$—O—CO—, —O—CO—$CH_2CH_2$—, —$CH_2$—O—CO—$CH_2$—, —$CH_2CH_2$—O—CO—, —O—CO—$CH_2$—$NR_4$—, or —O—CO—$CH_2$—O— bridge optionally substituted by one or two $C_{1-2}$-alkyl groups, wherein the heteroatoms of the bridge thereof are not bound at the 2 or 5 position of the pyrrolidine ring and are not bound at the 2 or 6 position of the piperidino ring, a piperazino or 4-($C_{1-4}$-alkyl)piperazino group wherein a hydrogen atom in the 2 position together with a hydrogen atom in the 3 position of the piperazino ring are replaced by a —$CH_2$—O—CO—$CH_2$— or —$CH_2CH_2$—O—CO— bridge optionally substituted by one or two $C_{1-2}$-alkyl groups, a piperazino group wherein a hydrogen atom in the 3 position together with the hydrogen atom in the 4 position are replaced by a —CO—O—$CH_2CH_2$— or —$CH_2$—O—CO—$CH_2$— bridge optionally substituted by one or two $C_{1-2}$-alkyl groups, wherein in each case the left-hand end of the bridge thereof is bound to the 3 position of the piperazino ring, a pyrrolidino, piperidino, or hexahydroazepino group substituted by $R_5$, a pyrrolidino group substituted in the 3 position by a 2-oxomorpholino group, wherein the 2-oxomorpholino group is optionally substituted by one or two $C_{1-2}$-alkyl groups, a piperidino or hexahydroazepino group substituted in the 3 or 4 position by a 2-oxomorpholino group, wherein the 2-oxomorpholino group is optionally substituted by one or two $C_{1-2}$-alkyl groups, a 4-($C_{1-4}$-alkyl)piperazino or 4-($C_{1-4}$-alkyl)-homopiperazino group substituted at a cyclic carbon atom by $R_5$, a piperazino or homopiperazino group substituted in the 4 position by $R_6$, a pyrrolidino group substituted in the 3 position by a ($R_4NR_6$), $R_6O$, $R_6S$, $R_6SO$, or $R_6SO_2$ group, a piperidino or hexahydroazepino group substituted in the 3 or 4 position by an ($R_4NR_6$), $R_6O$, $R_6S$, $R_6SO$, or $R_6SO_2$ group, a pyrrolidino, piperidino, or hexahydroazepino group substituted by a $R_5$—$C_{1-4}$-alkyl, ($R_4NR_6$)—$C_{1-4}$-alkyl, $R_6O$—$C_{1-4}$-alkyl, $R_6S$—$C_{1-4}$-alkyl, $R_6SO$—$C_{1-4}$-alkyl, $R_6SO_2$—$C_{1-4}$-alkyl, or $R_4NR_6$—CO group, a pyrrolidino group substituted in the 3 position by a $R_5$—CO—$NR_4$, $R_5$—$C_{1-4}$-alkylene-$CONR_4$, ($R_4N_6$)—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxomorpholino-$C_{1-4}$-alkylene-$CONR_4$, $R_5$—$C_{1-4}$-alkylene-Y, or $C_{2-4}$-alkyl-Y group, wherein the $C_{2-4}$-alkyl moiety of the $C_{2-4}$-alkyl-Y group is substituted from position 2 by a ($R_4NR_6$), $R_6O$, $R_6S$, $R_6SO$, or $R_6SO_2$ group and the 2-oxomorpholino moiety is optionally substituted by one or two $C_{1-2}$-alkyl groups, a piperidino or hexahydroazepino group substituted in the 3 or 4 position by a $R_5$—CO—$NR_4$, $R_5$—$C_{1-4}$-alkylene-$CONR_4$, ($R_4NR_6$)—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxomorpholino-$C_{1-4}$-alkylene-$CONR_4$, $R_5$—$C_{1-4}$-alkylene-Y, or $C_{2-4}$-alkyl-Y group, wherein the 2-oxomorpholino moiety is optionally substituted by one or two $C_{1-2}$-alkyl groups and the $C_{2-4}$-alkyl moiety of the $C_{2-4}$-alkyl-Y group is substituted from position 2 by a ($R_4NR_6$), $R_6O$, $R_6S$, $R_6SO$, or $R_6SO_2$ group, a 4-($C_{1-4}$-alkyl)piperazino or 4-($C_{1-4}$-alkyl)-homopiperazino group substituted at a cyclic carbon atom by an $R_5$—$C_{1-4}$-alkyl, ($R_4NR_6$)—$C_{1-4}$-alkyl, $R_6$—O—$C_{1-4}$-alkyl, $R_6S$—$C_{1-4}$-alkyl, $R_6SO$—$C_{1-4}$-alkyl, $R_6SO_2$—$C_{1-4}$-alkyl, or $R_4NR_6$—CO group, a piperazino or homopiperazino group substituted in the 4 position by an $R_5$—$C_{1-4}$-alkyl, $R_5$—CO, $R_5$—$C_{1-4}$-alkylene-CO, ($R_4NR_6$)—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, or $R_6SO_2$—$C_{1-4}$-alkylene-CO group, a piperazino or homopiperazino group substituted in the 4 position by a $C_{2-4}$-alkyl group, wherein the $C_{2-4}$-alkyl group is substituted from position 2 by an ($R_4NR_6$), $R_6O$, $R_6S$, $R_6SO$, or $R_6SO_2$ group, a pyrrolidino, piperidino, or hexahydroazepino group substituted by a 2-oxomorpholino-$C_{1-4}$-alkyl group, wherein the 2-oxomorpholino moiety is optionally substituted by one or two $C_{1-2}$-alkyl groups, a pyrrolidino group substituted in the 3 position by a $C_{2-4}$-alkyl-Y group, wherein the $C_{2-4}$-alkyl moiety of the $C_{2-4}$-alkyl-Y group is substituted from position 2 by a 2-oxomorpholino group optionally substituted by one or two $C_{1-2}$-alkyl groups, a piperidino or hexahydroazepino group substituted in the 3 or 4 position by a $C_{2-4}$-alkyl-Y group wherein the $C_{2-4}$-alkyl moiety of the $C_{2-4}$-alkyl-Y group is substituted from position 2 by a 2-oxomorpholino group optionally substituted by one or two $C_{1-2}$-alkyl groups, a 4-($C_{1-4}$-alkyl)piperazino or 4-($C_{1-4}$-alkyl)-homopiperazino group substituted at a cyclic carbon atom by a 2-oxomorpholino-$C_{1-4}$-alkyl group, wherein the 2-oxomorpholino moiety is optionally substituted by one or two $C_{1-2}$-alkyl groups, a piperazino or homopiperazino group substituted in the 4 position by a 2-oxomorpholino-$C_{1-4}$-alkylene-CO group, wherein the 2-oxomorpholino moiety is optionally substituted by one or two $C_{1-2}$-alkyl groups, a piperazino or homopiperazino group substituted in the 4 position by a $C_{2-4}$-alkyl group, wherein the $C_{2-4}$-alkyl moiety is substituted from position 2 by a 2-oxomorpholino group optionally substituted by one or two $C_{1-2}$-alkyl groups, a pyrrolidinyl or piperidinyl group substituted in the 1 position by $R_6$, by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO, or 2-oxomorpholino-$C_{1-4}$-alkylene-CO group, wherein the 2-oxomorpholino moiety is optionally substituted by one or two $C_{1-2}$-alkyl groups, a pyrrolidinyl or piperidinyl group substituted in the 1 position by a $C_{2-4}$-alkyl group, wherein the $C_{2-4}$-alkyl moiety is substituted from position 2 by an $(R_4NR_6)$, $R_6O$, $R_6S$, $R_6SO$, $R_6SO_2$, or 2-oxomorpholino group, wherein the 2-oxomorpholino moiety is optionally substituted by one or two $C_{1-2}$-alkyl groups, a pyrrolidin-3-yl-$NR_4$, piperidin-3-yl-$NR_4$, or piperidin-4-yl-$NR_4$ group substituted in each case at the cyclic nitrogen atom by $R_6$, by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO, or 2-oxomorpholino-$C_{1-4}$-alkylene-CO group, wherein the 2-oxomorpholino moiety is optionally substituted by one or two $C_{1-2}$-alkyl groups, a pyrrolidin-3-yl-$NR_4$, piperidin-3-yl-$NR_4$, or piperidin-4-yl-$NR_4$ group substituted in each case at the cyclic nitrogen atom by a $C_{2-4}$-alkyl group, wherein the $C_{2-4}$-alkyl moiety is substituted from position 2 by an $(R_4NR_6)$, $R_6O$, $R_6S$, $R_6SO$, $R_6SO_2$, or 2-oxomorpholino group, wherein the 2-oxomorpholino moiety is optionally substituted by one or two $C_{1-2}$-alkyl groups, a $R_5$—$C_{1-4}$-alkylene-$NP_4$ group, or a $C_{2-4}$-alkyl-$NR_4$-group, wherein the $C_{2-4}$-alkyl moiety is substituted from position 2 by an $(R_4NR_6)$, $R_6O$, $R_6S$, $R_6SO$, $R_6SO_2$, or 2-oxomorpholino group, wherein the 2-oxomorpholino moiety is optionally substituted by one or two $C_{1-2}$-alkyl groups, wherein:

D is a —$CH_2$—O—CO—$CH_2$—, —$CH_2CH_2$—O—CO—, —$CH_2$—O—CO—$CH_2CH_2$—, —$CH_2CH_2$—O—CO—$CH_2$—, or —$CH_2CH_2CH_2$—O—CO— bridge optionally substituted by one or two $C_{1-2}$-alkyl groups;

E is an —O—CO—$CH_2CH_2$—, —$CH_2$—O—CO—$CH_2$—, —$CH_2CH_2$—O—CO—, —O—CO—$CH_2CH_2CH_2$—, —$CH_2$—O—CO—$CH_2CH_2$—, —$CH_2CH_2$—O—CO—$CH_2$—, —$CH_2CH_2CH_2$—O—CO—, —O—CO—$CH_2$—$NR_4$—$CH_2$—, —$CH_2$—O—CO—$CH_2$—$NR_4$—, —O—CO—$CH_2$—O—$CH_2$—, or —$CH_2$—O—CO—$CH_2$—O— bridge optionally substituted by one or two $C_{1-2}$-alkyl groups;

$R_4$ is a hydrogen atom or a $C_{1-4}$-alkyl group;

$R_5$ is a 2-oxotetrahydrofuranyl, 2-oxotetrahydropyranyl, 2-oxo-1,4-dioxanyl, or 2-oxo-4-($C_{1-4}$-alkyl)-morpholinyl group optionally substituted by one or two $C_{1-2}$-alkyl groups; and $R_6$ is a 2-oxotetrahydrofuran-3-yl, 2-oxotetrahydrofuran-4-yl, 2-oxotetrahydropyran-3-yl, 2-oxotetrahydropyran-4-yl, or 2-oxotetrahydropyran-5-yl group optionally substituted by one or two $C_{1-2}$-alkyl groups, and Y is an oxygen or sulfur atom, or an imino, N-($C_{1-4}$-alkyl)-imino, sulfinyl, or sulfonyl group, and wherein the aryl moieties are phenyl groups which are each optionally mono- or disubstituted by R', wherein the substituents are identical or different, and R' is a fluorine, chlorine, bromine, or iodine atom, or a $C_{1-2}$-alkyl, trifluoromethyl, or $C_{1-2}$-alkoxy group, or two groups R', if they are bound to adjacent carbon atoms, are together a $C_{3-4}$-alkylene, methylenedioxy, or 1,3-butadien-1,4-ylene group, or a tautomer, stereoisomer, or salt thereof.

2. The compound of formula I according to claim 1, wherein:

X is a nitrogen atom;

$R_a$ is a hydrogen atom;

$R_b$ is a phenyl, benzyl, or 1-phenylethyl group, wherein the phenyl nucleus in each case is substituted by the groups $R_1$ to $R_3$, wherein $R_1$ and $R_2$, which are identical or different, are each a methyl group or a hydrogen, fluorine, chlorine, or bromine atom, and $R_3$ is a hydrogen atom;

$R_c$ is a hydrogen atom, $R_d$ is a hydrogen atom, or a methoxy, ethoxy, $C_{4-6}$-cycloalkoxy, $C_{3-6}$-cycloalkylmethoxy, 2-methoxyethoxy, 2-(cyclobutyloxy)ethoxy, 2-(cyclopentyloxy)ethoxy, 2-(cyclohexyloxy)ethoxy, 2-(cyclopropylmethoxy)ethoxy, tetrahydrofuran-3-yloxy, tetrahydropyran-4-yloxy, tetrahydrofuran-2-ylmethoxy, tetrahydrofuran-3-ylmethoxy, tetrahydropyran-2-ylmethoxy, or tetrahydropyran-4-ylmethoxy group;

A is a 1,2-vinylene group;

B is a methylene or ethylene group or, if B is bound to a carbon atom of C, it is optionally a bond; and C is a pyrrolidino group wherein the two hydrogen atoms in the 3 position are replaced by E, a piperidino group wherein the two hydrogen atoms in the 3 position or in the 4 position are replaced by E, a pyrrolidino or piperidino group wherein two vicinal hydrogen atoms are replaced by an —O—CO—$CH_2$—, —$CH_2$—O—CO—, —O—CO—$CH_2$—$NR_4$—, or —O—CO—$CH_2$—O— bridge optionally substituted by one or two methyl groups, wherein the heteroatoms of the bridge thereof are not bound at the 2 or 5 position of the pyrrolidine ring and are not bound at the 2 or 6 position of the piperidino ring, a piperazino group wherein a hydrogen atom in the 3 position together with the hydrogen atom in the 4 position are replaced by a —CO—O—$CH_2CH_2$— or —$CH_2$—O—CO—$CH_2$— bridge optionally substituted by one or two methyl groups, wherein in each case the left-hand end of the abovementioned bridges is bound to the 3 position of the piperazino ring, a pyrrolidino or piperidino group substituted by $R_5$, a pyrrolidino group substituted in the 3 position by a 2-oxomorpholino group, wherein the 2-oxomorpholino group is optionally substituted by one or two methyl groups, a piperidino group substituted in the 3 or 4 position by a 2-oxomorpholino group, wherein the 2-oxomorpholino group is optionally substituted by one or two methyl groups, a piperazino group substituted in the 4 position by $R_6$, a pyrrolidino group substituted in the 3 position by an $(R_4NR_6)$, $R_6O$, $R_6S$, $R_6SO$, or $R_6SO_2$ group, a piperidino group substituted in the 3 or 4 position by an $(R_4NR_6)$, $R_6O$, $R_6S$, $R_6SO$, or $R_6SO_2$ group, a pyrrolidino or piperidino group substituted by an $(R_4NR_6)$—$C_{1-2}$-alkyl, $HNR_6$—CO, or $R_4NR_6$—CO group, a pyrrolidino group substituted in the 3 position by an $R_5$—CO—NH or $R_5$—CO—$NR_4$ group, a piperidino group substituted in the 3 or 4 position by an $R_5$—CO—NH or $R_5$—CO—$NR_4$ group, a piperazino group substituted in the 4 position by an $R_5$—$C_{1-2}$-alkyl, $R_5$—CO, $R_5$—$C_{1-2}$-alkylene-CO, $(R_4NR_6)$—$C_{1-2}$-alkylene-CO, $R_6O$—$C_{1-2}$-alkylene-CO, $R_6S$—$C_{1-2}$-alkylene-CO, $R_6SO$—$C_{1-2}$-alkylene-CO, or $R_6SO_2$—$C_{1-2}$-alkylene-CO group, a piperazino group substituted in the 4 position by a $C_{2-3}$-alkyl group, wherein the $C_{2-3}$-alkyl group is substituted from position 2 by an $(R_4NR_6)$, $R_6O$, $R_6S$, $R_6SO$, or $R_6SO_2$ group, a pyrrolidino or piperidino group substituted by a 2-oxomorpholino-$C_{1-2}$-alkyl group, wherein the 2-oxomorpholino moiety is optionally substituted by one or two methyl groups, a piperazino group substituted in the 4 position by a 2-oxomorpholino-$C_{1-2}$-alkylene-CO group, wherein the 2-oxomorpholino moiety is optionally substituted by one or two methyl groups, a piperazino group substituted in the 4 position by a $C_{2-3}$-alkyl group, wherein the $C_{2-3}$-alkyl moiety is substituted from position 2 by a 2-oxomorpholino group optionally substituted by one or two methyl groups, a piperidinyl group substituted in the 1 position by $R_6$, by an $R_5$—$C_{1-2}$-alkyl, $R_5$—CO, $R_5$—$C_{1-2}$-alkylene-CO, $(R_4NR_6)$—$C_{1-2}$-alkylene-CO, $R_6O$—$C_{1-2}$-alkylene-CO, $R_6S$—$C_{1-2}$-alkylene-CO, $R_6SO$—$C_{1-2}$-alkylene-CO, $R_6SO_2$—$C_{1-2}$-alkylene-CO, or 2-oxomorpholino-$C_{1-2}$-alkylene-CO group, wherein the 2-oxomorpholino moiety is optionally substituted by one or two methyl groups, a piperidinyl group substituted in the 1 position by a $C_{2-3}$-alkyl group, wherein the $C_{2-3}$-alkyl moiety is substituted from position 2 by an $(R_4NR_6)$, $R_6O$, $R_6S$, $R_6SO$, $R_6SO_2$, or 2-oxomorpholino group, wherein the 2-oxomorpholino moiety is optionally substituted by one or two methyl groups, a pyrrolidin-3-yl-$NR_4$, piperidin-3-yl-$NR_4$, or piperidin-4-yl-$NR_4$ group substituted in each case at the cyclic nitrogen atom by $R_6$, by an $R_5$—$C_{1-2}$-alkyl, $R_5$—CO, $R_5$—$C_{1-2}$-alkylene-CO, $(R_4NR_6)$—$C_{1-2}$-alkylene-CO, $R_6O$—$C_{1-2}$-alkylene-CO, $R_6S$—$C_{1-2}$-alkylene-CO, $R_6SO$—$C_{1,3}$-alkylene-CO, $R_6SO_2$—$C_{1-2}$-alkylene-CO, or 2-oxomorpholino-$C_{1-2}$-alkylene-CO group, wherein the 2-oxomorpholino moiety is optionally substituted by one or two methyl groups, or a pyrrolidin-3-yl-$NR_4$, piperidin-3-yl-$NR_4$, or piperidin-4-yl-$NR_4$ group substituted in each case at the cyclic nitrogen atom by a $C_{2-3}$-alkyl group, wherein the $C_{2-3}$-alkyl moiety is substituted from position 2 by an $(R_4NR_6)$, $R_6O$, $R_6S$, $R_6SO$, $R_6SO_2$, or 2-oxomorpholino group, wherein the 2-oxomorpholino moiety is optionally substituted by one or two methyl groups, wherein:
E is an —O—CO—$CH_2CH_2$—, —$CH_2$—O—CO—$CH_2$—, —$CH_2CH_2$—O—CO—, —$CH_2CH_2$—O—CO—$CH_2$—, —O—CO—$CH_2$—$NR_4$—$CH_2$—, —$CH_2$—O—CO—$CH_2$—$NR_4$—, —O—CO—$CH_2$—O—$CH_2$—, or —$CH_2$—O—CO—$CH_2$—O— bridge optionally substituted by one or two methyl groups;

$R_4$ is a methyl or ethyl group;

$R_5$ is a 2-oxotetrahydrofuranyl, 2-oxo-1,4-dioxanyl, or 2-oxo-4-($C_{1-4}$-alkyl)-morpholinyl group optionally substituted by one or two methyl groups; and $R_6$ is a 2-oxotetrahydrofuran-3-yl or 2-oxotetrahydrofuran-4-yl group optionally substituted by one or two methyl groups, or a tautomer, stereoisomer, or salt thereof.

3. The compound of formula I according to claim 1, wherein:

X is a nitrogen atom;

$R_a$ is a hydrogen atom;

$R_b$ is a phenyl, benzyl, or 1-phenylethyl group, wherein the phenyl nucleus in each case is substituted by $R_1$ to $R_3$, wherein $R_1$ and $R_2$, which are identical or different, are each a methyl group or a hydrogen, fluorine, chlorine, or bromine atom, and $R_3$ is a hydrogen atom;

$R_c$ is a hydrogen atom;

$R_d$ is a hydrogen atom, or a methoxy, ethoxy, $C_{4-6}$-cycloalkoxy, $C_{3-6}$-cycloalkylmethoxy, 2-methoxyethoxy, 2-(cyclobutyloxy)ethoxy, 2-(cyclopentyloxy)ethoxy, 2-(cyclohexyloxy)ethoxy, 2-(cyclopropylmethoxy)ethoxy, tetrahydrofuran-3-yloxy, tetrahydropyran-4-yloxy, tetrahydrofuran-2-ylmethoxy, tetrahydrofuran-3-ylmethoxy, tetrahydropyran-2-ylmethoxy, or tetrahydropyran-4-ylmethoxy group;

A is a 1,2-vinylene group;

B is a methylene or ethylene group or, if B is bound to a carbon atom of C, it is optionally a bond; and C is a piperidino group wherein the two hydrogen atoms in the 4 position are replaced by a —$CH_2$—O—CO—$CH_2$—, —$CH_2CH_2$—O—CO—, —$CH_2CH_2$—O—CO—$CH_2$—, —O—CO—$CH_2$—$NCH_3$—$CH_2$—, or —O—CO—$CH_2$—O—$CH_2$— bridge, a piperazino group wherein a hydrogen atom in the 3 position together with the hydrogen atom in the 4 position are replaced by a —CO—O—$CH_2$—$CH_2$— or —$CH_2$—O—CO—$CH_2$— bridge, wherein in each case the left-hand end of the bridge thereof is bound to the 3 position of the piperazino ring, a piperidino group substituted by a 2-oxotetrahydrofuranyl group, a piperidino group substituted in the 4 position by a 2-oxomorpholino or 2-oxomorpholinomethyl group, wherein the 2-oxomorpholino moiety is optionally substituted by one or two methyl groups, a piperazino group substituted in the 4 position by a 2-oxotetrahydrofuran-3-yl or 2-oxotetrahydrofuran-4-yl group, a piperidino group substituted in the 4 position by $CH_3NR_6$ or $R_6S$ group, a piperazino group substituted in the 4 position by a 2-oxotetrahydrofuranylmethyl or 2-oxotetrahydrofuranylcarbonyl group, a piperazino group substituted in the 4 position by a straight-chained $C_{2-3}$-alkyl group, wherein the $C_{2-3}$- alkyl moiety is terminally substituted by a 2-oxotetrahydrofuran-3-ylsulfenyl group, a piperidin-4-yl group substituted in the 1 position by a 2-oxotetrahydrofuran-3-yl or 2-oxotetrahydrofuran-4-yl group, or a piperidin-4-yl-$NCH_3$ group substituted at the cyclic nitrogen atom by a 2-oxotetrahydrofuran-3-yl, 2-oxotetrahydrofuran-4-yl, or 2-oxotetrahydrofuranylcarbonyl group, wherein:

$R_6$ is a 2-oxotetrahydrofuran-3-yl or 2-oxotetrahydrofuran-4-yl group, or a tautomer, stereoisomer, or salt thereof.

4. The compound of formula I according to claim 1, wherein:

X is a nitrogen atom;

$R_a$ is a hydrogen atom;

$R_b$ is a 1-phenylethyl group or a phenyl group substituted by $R_1$ to $R_3$, wherein $R_1$ and $R_2$, which are identical or different, are each a methyl group or a hydrogen, fluorine, chlorine, or bromine atom, and $R_3$ is a hydrogen atom;

$R_c$ is a hydrogen atom;

$R_d$ is a hydrogen atom, or a methoxy, ethoxy, 2-methoxyethoxy, cyclobutyloxy, cyclopentyloxy, cyclopropylmethoxy, cyclobutylmethoxy, tetrahydrofuran-3-yloxy, tetrahydropyran-4-yloxy, or tetrahydrofuran-2-ylmethoxy group, A is a 1,2-vinylene group;

B is a methylene group or, if B is bound to a carbon atom of C, it is optionally a bond; and C is a piperidino group wherein the two hydrogen atoms are replaced in the 4 position by a —$CH_2$—O—CO—$CH_2$—, —$CH_2CH_2$—O—CO—, —$CH_2CH_2$—O—CO—$CH_2$—, —O—CO—$CH_2$—$NCH_3$—$CH_2$—, or —O—CO—$CH_2$—O—$CH_2$— bridge, a piperazino group wherein a hydrogen atom in the 3 position together with the hydrogen atom in the 4 position are replaced by a —CO—O—$CH_2$—$CH_2$— or —$CH_2$—O—CO—$CH_2$— bridge, wherein in each case the left-hand end of the bridge thereof is bound to the 3 position of the piperazino ring, a piperidino group substituted by a 2-oxotetrahydrofuranyl group, a piperidino group substituted in the 4 position by a 2-oxomorpholino or 2-oxomorpholinomethyl group, wherein the 2-oxomorpholino moiety is optionally substituted by one or two methyl groups, a piperazino group substituted in the 4 position by a 2-oxotetrahydrofuran-3-yl or 2-oxotetrahydrofuran-4-yl group, a piperidino group substituted in the 4 position by a $CH_3NR_6$ or $R_6S$ group, a piperazino group substituted in the 4 position by a 2-oxotetrahydrofuranylmethyl or 2-oxotetrahydrofuranylcarbonyl group, a piperazino group substituted in the 4 position by a [2-(2-oxotetrahydrofuran-3-ylsulfenyl)ethyl] group, a piperidin-4-yl group substituted in the 1 position by a 2-oxotetrahydrofuran-3-yl or 2-oxotetrahydrofuran-4-yl group, or a piperidin-4-yl-$NCH_3$ group substituted at the cyclic nitrogen atom by a 2-oxotetrahydrofuran-3-yl, 2-oxotetrahydrofuran-4-yl, or 2-oxotetrahydrofuranylcarbonyl group, wherein:

$R_6$ is a 2-oxotetrahydrofuran-3-yl or 2-oxotetrahydrofuran-4-yl group, or a tautomer, stereoisomer, or salt thereof.

5. A compound selected from the group consisting of:

(a) 4-[(3-chloro-4-fluorophenyl)amino]-6-({4-[4-(2-oxotetrahydrofuran-3-yl)piperazin-1-yl]-1-oxo-2-buten-1-yl}amino)-7-cyclopropylmethoxyquinazoline;

(b) 4-[(3-chloro-4-fluorophenyl)amino]-6-({4-[4-(2-oxotetrahydrofuran-4-yl)piperazine-1yl]-1-oxo-2-buten-1-yl}amino)-7-cyclopropylmethoxyquinazoline;

(c) 4-[(3-chloro-4-fluorophenyl)amino]-6-{[4-(4-{2-[(2-oxotetrahydrofuran-3-yl)sulfanyl]ethyl}piperazin-1-yl)-1-oxo-2-buten-1-yl]amino}-7-cyclopropylmethoxyquinazoline;

(d) 4-[(3-chloro-4-fluorophenyl)amino]-6-{[4-(3-oxoperhydropyrazino[2,1-c][1,4]oxazin-8-yl)-1-oxo-2-buten-1-yl]amino}-7-cyclopropylmethoxyquinazoline;

(e) (S)-4-[(3-chloro-4-fluorophenyl)amino]-6-[(4-{4-[(5-oxotetrahydrofuran-2-yl)carbonyl]piperazin-1-yl}-1-oxo-2-buten-1-yl)amino]-7-cyclopropylmethoxyquinazoline;

(f) 4-[(3-chloro-4-fluorophenyl)amino]-6-{[4-(1-oxoperhydropyrazino[2,1-c][1,4]oxazin-8-yl)-1-oxo-2-buten-1-yl]amino}-7-cyclopropylmethoxyquinazoline; and (g) 4-[(3-chloro-4-fluorophenyl)amino]-6-[(4-{4-[(2-oxotetrahydrofuran-3-yl)sulfanyl]piperidin-1-yl}-1-oxo-2-buten-1-yl)amino]-7-cyclopropylmethoxyquinazoline, or a salt thereof.

6. A physiologically acceptable salt of the compound according to any one of claims 1 to 5.

7. A pharmaceutical composition comprising the compound according to any one of claims 1 to 5 or the physiologically acceptable salt according to claim 6.

8. The pharmaceutical composition according to claim 7, further comprising one or more inert carriers and/or diluents.

9. A method for the treatment or prophylaxis of benign or malignant tumors, polyps, and diseases of the respiratory tract, lungs, gastrointestinal tract, bile duct, gall bladder, kidneys, and skin which comprises administering to a host in need of such treatment an effective amount of a compound in accordance with any one of claims 1 to 6.

* * * * *